(12) United States Patent
Kreutzer et al.

(10) Patent No.: US 9,133,454 B2
(45) Date of Patent: Sep. 15, 2015

(54) METHOD AND MEDICAMENT FOR INHIBITING THE EXPRESSION OF A GIVEN GENE

(71) Applicant: Alnylam Pharmaceuticals, Inc., Cambridge, MA (US)

(72) Inventors: Roland Kreutzer, Weidenberg (DE); Stefan Limmer, Kulmbach (DE)

(73) Assignee: Alnylam Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 14/218,476

(22) Filed: Mar. 18, 2014

(65) Prior Publication Data

US 2014/0220113 A1 Aug. 7, 2014

Related U.S. Application Data

(60) Continuation of application No. 13/656,513, filed on Oct. 19, 2012, now Pat. No. 8,877,726, which is a continuation of application No. 11/982,325, filed on Oct. 31, 2007, now abandoned, which is a continuation of application No. 10/612,179, filed on Jul. 2, 2003, now Pat. No. 8,202,980, which is a division of application No. 09/889,802, filed as application No. PCT/DE00/00244 on Jan. 29, 2000, now abandoned.

(30) Foreign Application Priority Data

Jan. 30, 1999 (DE) .................................. 199 03 713
Nov. 24, 1999 (DE) .................................. 199 56 568

(51) Int. Cl.
*C12N 15/113* (2010.01)
*A61K 31/713* (2006.01)
*C12N 15/11* (2006.01)
*A61K 38/00* (2006.01)

(52) U.S. Cl.
CPC ............ *C12N 15/113* (2013.01); *A61K 31/713* (2013.01); *C12N 15/111* (2013.01); *A61K 38/00* (2013.01); *C12N 2310/111* (2013.01); *C12N 2310/14* (2013.01); *C12N 2310/53* (2013.01); *C12N 2330/30* (2013.01)

(58) Field of Classification Search
None
See application file for complete search history.

(56) References Cited

U.S. PATENT DOCUMENTS

| | | |
|---|---|---|
| 4,868,116 A | 9/1989 | Morgan et al. |
| 4,980,286 A | 12/1990 | Morgan et al. |
| 4,987,071 A | 1/1991 | Cech et al. |
| 5,107,065 A | 4/1992 | Shewmaker et al. |
| 5,112,734 A | 5/1992 | Kramer et al. |
| 5,190,931 A | 3/1993 | Inouye |
| 5,208,149 A | 5/1993 | Inouye |
| 5,212,295 A | 5/1993 | Cook |
| 5,225,347 A | 7/1993 | Goldberg et al. |
| 5,246,921 A | 9/1993 | Reddy et al. |
| 5,254,678 A | 10/1993 | Haseloff et al. |
| 5,328,470 A | 7/1994 | Nabel et al. |
| 5,496,698 A | 3/1996 | Draper et al. |
| 5,521,302 A | 5/1996 | Cook |
| 5,525,468 A | 6/1996 | McSwiggen |
| 5,574,142 A | 11/1996 | Meyer, Jr. et al. |
| 5,587,361 A | 12/1996 | Cook et al. |
| 5,616,459 A | 4/1997 | Kramer et al. |
| 5,624,803 A | 4/1997 | Noonberq et al. |
| 5,635,385 A | 6/1997 | Leopold et al. |
| 5,639,655 A | 6/1997 | Thompson et al. |
| 5,674,683 A | 10/1997 | Kool |
| 5,683,873 A | 11/1997 | George et al. |
| 5,703,054 A | 12/1997 | Bennett et al. |
| 5,712,257 A | 1/1998 | Carter |
| 5,719,271 A | 2/1998 | Cook et al. |
| 5,731,181 A | 3/1998 | Kmiec |
| 5,739,271 A | 4/1998 | Sridhar et al. |
| 5,789,230 A | 8/1998 | Cotton et al. |
| 5,801,154 A | 9/1998 | Baracchini et al. |
| 5,811,275 A | 9/1998 | Wong-Staal et al. |
| 5,811,300 A | 9/1998 | Sullivan et al. |
| 5,814,500 A | 9/1998 | Dietz |
| 5,824,519 A | 10/1998 | Norris et al. |
| 5,837,510 A | 11/1998 | Goldsmith et al. |
| 5,854,067 A | 12/1998 | Newgard et al. |
| 5,864,028 A | 1/1999 | Sioud |
| 5,866,701 A | 2/1999 | Hampel et al. |
| 5,891,717 A | 4/1999 | Newgard et al. |
| 5,898,031 A | 4/1999 | Crooke |
| 5,908,779 A | 6/1999 | Carmichael et al. |
| 5,939,262 A | 8/1999 | Pasloske et al. |
| 5,968,737 A | 10/1999 | Ah-Osman et al. |

(Continued)

FOREIGN PATENT DOCUMENTS

AU 717543 B2 12/1997
AU 2000-32713 B2 8/2000

(Continued)

OTHER PUBLICATIONS

Ichim et al., "RNA Interference A Potent Tool for Gene-Specific Therapeutics" American Journal of Transplantation, 2004, pp. 1227-1236, vol. 4.

(Continued)

*Primary Examiner* — Tracy Vivlemore
(74) *Attorney, Agent, or Firm* — Fenwick & West LLP

(57) ABSTRACT

The invention relates to an isolated RNA that mediates RNA interference of an mRNA to which it corresponds and a method of mediating RNA interference of mRNA of a gene in a cell or organism using the isolated RNA.

16 Claims, 5 Drawing Sheets

(56) References Cited

U.S. PATENT DOCUMENTS

Figure 1:
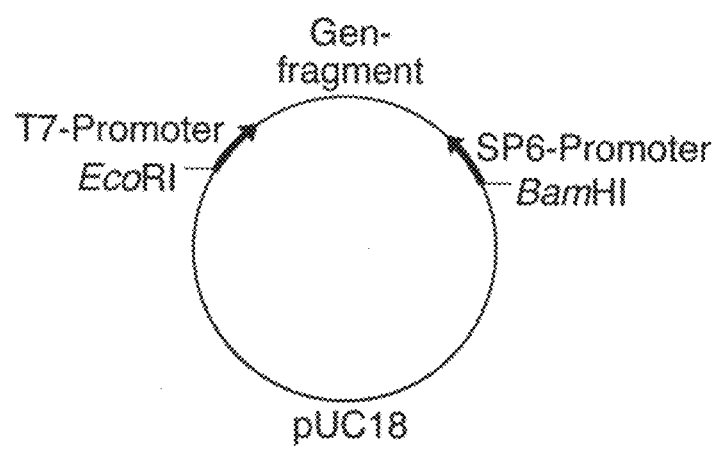

| | | |
|---|---|---|
| 5,985,620 A | 11/1999 | Sioud |
| 5,998,203 A | 12/1999 | Matulic-Adamic et al. |
| 6,025,167 A | 2/2000 | Cech et al. |
| 6,054,299 A | 4/2000 | Conrad |
| 6,057,156 A | 5/2000 | Akhtar et al. |
| 6,071,890 A | 6/2000 | Scheule et al. |
| 6,077,705 A | 6/2000 | Duane et al. |
| 6,080,851 A | 6/2000 | Pachuk et al. |
| 6,087,164 A | 7/2000 | Hochberg et al. |
| 6,087,172 A | 7/2000 | Veerapaneni et al. |
| 6,099,823 A | 8/2000 | Falb |
| 6,100,087 A | 8/2000 | Rossi et al. |
| 6,100,444 A | 8/2000 | Frelinger et al. |
| 6,107,094 A | 8/2000 | Crooke |
| 6,127,533 A | 10/2000 | Cook et al. |
| 6,166,197 A | 12/2000 | Cook et al. |
| 6,183,959 B1 | 2/2001 | Thompson |
| 6,225,291 B1 | 5/2001 | Lewin et al. |
| 6,245,560 B1 | 6/2001 | Lisziewicz |
| 6,245,748 B1 | 6/2001 | Wellstein et al. |
| 6,255,071 B1 | 7/2001 | Beach et al. |
| 6,271,358 B1 | 8/2001 | Manoharan et al. |
| 6,346,398 B1 | 2/2002 | Pavco et al. |
| 6,355,415 B1 | 3/2002 | Wagner et al. |
| 6,423,489 B1 | 7/2002 | Anderson et al. |
| 6,482,803 B1 | 11/2002 | Ruth et al. |
| 6,486,299 B1 | 11/2002 | Shimkets et al. |
| 6,506,559 B1 | 1/2003 | Fire et al. |
| 6,573,046 B1 | 6/2003 | Kmiec et al. |
| 7,196,184 B2 | 3/2007 | Heidenreich et al. |
| 7,198,814 B2 | 4/2007 | Endo et al. |
| 7,348,314 B2 | 3/2008 | John et al. |
| 7,473,525 B2 | 1/2009 | Kreutzer et al. |
| 7,745,418 B2 | 6/2010 | John et al. |
| 7,763,590 B2 | 7/2010 | Kreutzer et al. |
| 7,829,693 B2 | 11/2010 | Kreutzer et al. |
| 7,846,907 B2 | 12/2010 | Heidenreich et al. |
| 7,994,309 B2 | 8/2011 | Kreutzer et al. |
| 8,101,584 B2 | 1/2012 | Kreutzer et al. |
| 8,101,742 B2 | 1/2012 | Kreutzer et al. |
| 8,114,851 B2 | 2/2012 | Kreutzer et al. |
| 8,114,981 B2 | 2/2012 | Kreutzer et al. |
| 8,119,608 B2 | 2/2012 | Kreutzer et al. |
| 8,168,776 B2 | 5/2012 | Kreutzer et al. |
| 8,183,362 B2 | 5/2012 | Kreutzer et al. |
| 8,202,980 B2 | 6/2012 | Kreutzer et al. |
| 8,273,868 B2 | 9/2012 | John et al. |
| 8,273,870 B2 | 9/2012 | Kreutzer et al. |
| 8,546,143 B2 | 10/2013 | Kreutzer et al. |
| 2002/0086356 A1 | 7/2002 | Tuschl et al. |
| 2002/0114784 A1 | 8/2002 | Li et al. |
| 2002/0123034 A1 | 9/2002 | Canaani et al. |
| 2002/0132346 A1 | 9/2002 | Cibelli |
| 2002/0162126 A1 | 10/2002 | Beach et al. |
| 2002/0173478 A1 | 11/2002 | Gewirtz |
| 2003/0027783 A1 | 2/2003 | Zernicka-Goetz et al. |
| 2003/0108923 A1 | 6/2003 | Tuschl et al. |
| 2003/0125281 A1 | 7/2003 | Lewis et al. |
| 2003/0134808 A1 | 7/2003 | Wengel |
| 2003/0143732 A1 | 7/2003 | Fosnaugh et al. |
| 2003/0148341 A1 | 8/2003 | Sin et al. |
| 2003/0157030 A1 | 8/2003 | Davis et al. |
| 2003/0176671 A1 | 9/2003 | Reed et al. |
| 2003/0180756 A1 | 9/2003 | Shi et al. |
| 2003/0190635 A1 | 10/2003 | McSwiggen |
| 2003/0198627 A1 | 10/2003 | Arts et al. |
| 2004/0001811 A1 | 1/2004 | Kreutzer et al. |
| 2004/0053875 A1 | 3/2004 | Kreutzer et al. |
| 2004/0072779 A1 | 4/2004 | Kreutzer et al. |
| 2004/0102408 A1 | 5/2004 | Kreutzer et al. |
| 2006/0258608 A1 | 11/2006 | Meyers |
| 2008/0166800 A1 | 7/2008 | Kreutzer et al. |
| 2008/0171862 A1 | 7/2008 | Kreutzer et al. |
| 2008/0182981 A1 | 7/2008 | Kreutzer et al. |
| 2008/0233651 A1 | 9/2008 | Kreutzer et al. |
| 2008/0261303 A1 | 10/2008 | Kreutzer et al. |

FOREIGN PATENT DOCUMENTS

| | | |
|---|---|---|
| AU | 778474 | 8/2000 |
| AU | 2005-201044 B2 | 4/2005 |
| DE | 19618797 A1 | 10/1996 |
| DE | 196-18-797 C2 | 11/1997 |
| DE | 196-31-919 C2 | 7/1998 |
| DE | 199 03 713.2 | 1/1999 |
| DE | 199 56 568.6 | 11/1999 |
| DE | 199 56 568 A1 | 11/1999 |
| DE | 200-23125 U1 | 1/2000 |
| DE | 101-00588 A1 | 1/2001 |
| DE | 1016-3098 A1 | 12/2001 |
| DE | 101-00-586 C1 | 4/2002 |
| DE | 102-30996 A1 | 7/2002 |
| DE | 102-30997 A1 | 7/2002 |
| DE | 102-35-620.3 | 8/2002 |
| DE | 69233117 D1 | 4/2004 |
| DE | 100-80-167 B4 | 3/2008 |
| DE | 100-66235 B4 | 4/2008 |
| DE | 10066235 B4 | 4/2008 |
| EP | 1214945 A2 | 1/2000 |
| EP | 1144623 B1 | 8/2002 |
| EP | 1230-375 B1 | 7/2005 |
| EP | 1550719 A1 | 7/2005 |
| EP | 1550719 B1 | 12/2008 |
| GB | 9927444.1 | 11/1999 |
| JP | H07-504438 | 5/1995 |
| JP | 2004-526422 | 9/2004 |
| WO | WO 89/02468 | 3/1989 |
| WO | WO-89/05345 | 6/1989 |
| WO | WO-89/07136 | 8/1989 |
| WO | WO-92/07573 | 5/1992 |
| WO | WO 92/19732 | 11/1992 |
| WO | WO 94/01550 A1 | 1/1994 |
| WO | WO-96/017057 | 6/1996 |
| WO | WO-97/05266 A1 | 2/1997 |
| WO | WO 97/043431 | 11/1997 |
| WO | WO 98/05770 A2 | 2/1998 |
| WO | WO-98/53083 A1 | 11/1998 |
| WO | WO-99/15682 A2 | 4/1999 |
| WO | WO-99/32619 | 7/1999 |
| WO | WO-99/49029 A1 | 9/1999 |
| WO | WO-99/53050 A1 | 10/1999 |
| WO | WO-99/54459 | 10/1999 |
| WO | WO-99/61631 | 12/1999 |
| WO | WO-00/01846 | 1/2000 |
| WO | WO-00/22113 | 4/2000 |
| WO | WO-00/22114 | 4/2000 |
| WO | WO-00/44495 A1 | 8/2000 |
| WO | WO-00/44895 | 8/2000 |
| WO | WO-00/44895 A1 | 8/2000 |
| WO | WO-00/44914 | 8/2000 |
| WO | WO 00/63364 A2 | 10/2000 |
| WO | WO-00/68374 | 11/2000 |
| WO | WO-01/18197 A1 | 3/2001 |
| WO | WO-01/29058 A1 | 4/2001 |
| WO | WO-01/36646 | 4/2001 |
| WO | WO-01/36646 A1 | 5/2001 |
| WO | WO-01/42443 | 6/2001 |
| WO | WO-01/48183 A2 | 7/2001 |
| WO | WO-01/68836 A2 | 9/2001 |
| WO | WO-01/70949 A1 | 9/2001 |
| WO | WO-01/75164 A2 | 10/2001 |
| WO | WO-01/92513 A1 | 12/2001 |
| WO | WO-02/16620 A2 | 2/2002 |
| WO | WO-02/26780 A2 | 4/2002 |
| WO | WO-02/44321 A2 | 6/2002 |
| WO | WO-02/055692 A2 | 7/2002 |
| WO | WO-02/055693 A2 | 7/2002 |
| WO | WO-02/061034 A2 | 8/2002 |
| WO | WO-02/068635 A2 | 9/2002 |
| WO | WO-02/068637 A2 | 9/2002 |
| WO | WO-03/006477 A1 | 1/2003 |
| WO | WO-03/012052 A2 | 2/2003 |

(56) References Cited

FOREIGN PATENT DOCUMENTS

| | | |
|---|---|---|
| WO | WO-03/012082 A2 | 2/2003 |
| WO | WO-03/016572 A1 | 2/2003 |
| WO | WO-03/033700 A1 | 4/2003 |
| WO | WO-03/035082 A1 | 5/2003 |
| WO | WO-03/035083 A1 | 5/2003 |
| WO | WO-03/035868 A1 | 5/2003 |
| WO | WO-03/035869 A1 | 5/2003 |
| WO | WO-03/035870 A1 | 5/2003 |
| WO | WO-03/035876 A1 | 5/2003 |
| WO | WO-03/040366 | 5/2003 |
| WO | WO-03/070283 A2 | 8/2003 |
| WO | WO-03/070750 A2 | 8/2003 |
| WO | WO-03/070969 A2 | 8/2003 |
| WO | WO-03/070972 A2 | 8/2003 |
| WO | WO-03/074654 A2 | 9/2003 |
| WO | WO-03/080794 A2 | 10/2003 |
| WO | WO-03/080807 A2 | 10/2003 |
| WO | WO 2004/015107 | 2/2004 |
| WO | WO 2004/027030 | 4/2004 |
| WO | WO-2004/045543 | 6/2004 |
| WO | WO-2004/065601 | 6/2004 |
| WO | WO-2004/065601 | 8/2004 |
| WO | WO-2005/012357 | 2/2005 |
| WO | WO-2007/115168 A2 | 10/2007 |

OTHER PUBLICATIONS

Japanese Patent Office, Office Action for JP Application No. 2009-285705, Jan. 13, 2015, 5 pages.
Submission by Abbott Laboratories in the opposition proceedings of European Patent No. 1 214 945 (Nov. 20, 2008).
Submission by Abbott Laboratories in the opposition proceedings of European Patent No. 1 214 945 (Oct. 30, 2007).
Notice of opposition by Abbott Laboratories against European Patent No. 1 214 945 (Mar. 8, 2006).
Agami, "RNAi and related mechanisms and their potential use for therapy" Current Opin. in Chemical Biology 6:829-834, 2002.
Agrawal et al., 1995, 105-21, Editors: Akhtar, Saghir, Publisher CRC.
Agrawal et al., "Antisense therapeutics: is it as simple as complementary base recognition," Molecular Medicine, 6:72-81 (2000).
Agrawal, S., "Antisense oligonucleotides: towards clinical trials," Tibtech (1996), 14: 376-387.
Agrawal et al., "Self-Stabilized Oligonucleoticks as Novel Antisense Agents," Delivery Strategies for Antisepse Oligonucleotide Themoeutics. Edited by Saghir Akhtar, CRC Press, pp. 105-121 (1995).
Agrawal, S., et al., "Oligodeoxynucleoside phosphoramidates and phosphorothioates as inhibitors of human immunodeficiency virus," Proc. Natl. Acad. Sci. USA (1988), 85:7079-7083.
Agrawal, S., et al., "Protocols for Oligonucleotides and Analogs," Chapters 5 and 6, 1993, pp. 81-140, Humana Press, Totowa, NH.
Written Submission by Alexandra Oppl in Opposition proceedings for DE 100 80 167.6 (Mar. 4, 2009).
Notice of Opposition by Alexandra Oppl against DE 100 80 167.6 (Jun. 20, 2008).
Alfonzo et al., "The mechanism of U insertion/deletion RNA editing in kinetoplastid mitochondria," Nucleic Acid Research, 25:3751-3759 (1997).
Submission by Alnylam Europe in opposition proceedings for European Patent No. 1144623 (Dec. 7, 2004), 140 pages.
Submission by Alnylam Europe in opposition proceedings for European Patent No. 1144623 (Apr. 21, 2006), 63 pages.
Response to the Submission of Opponent 1, filed by Alnylam Europe AG on Nov. 17, 2011, Opposition against European Patent EP 1550719, 17 Pages.
Response to Submissions of Opponent 1 dated Aug. 16, 2011, filed with the European Patent Office by Patentee Alnylam Europe AG on Mar. 6, 2012 in Opposition against European Patent No. EP 1214945, 14 Pages.
Response to Summons to Attend Oral proceedings issued by the German Patent and Trademark office on Dec. 9, 2009 regarding opposition against German Patent DE 10066235.8, filed by Alnylam Europe AG and Jan. 4, 2010, 36 Pages.
Grounds of Appeal filed by Alnylam Europe AG for European Patent EP 1214945, filed Aug. 5, 2009, 21 pages.
Written Submission by Alnylam Europe AG in Opposition proceedings for DE 100 80 167.6 (Mar. 4, 2009) (translation attached).
Patentee's Observations submitted by Alnylam Europe AG in Opposition proceedings for DE 100 80 167.6 (Dec. 18, 2008).
Patentee's Observations submitted by Alnylam Europe AG in Opposition proceedings for DE 100 66 235.6 (Feb. 4, 2009) (translation attached).
Decision to revoke European Patent EP 1144623 of Alnylam Europe AG, Dec. 9, 2008, 50 Pages.
Decision and Minutes in opposition proceedings for European Patent No. 12 14 945 (Mar. 31, 2009). (translation attached).
Decision to revoke European Patent EP 1214945 of Alnylam Europe AG, Jan. 20, 2009, 56 Pages.
Decision to revoke European Patent EP 10080167 of Alnylam Europe AG, Mar. 18, 2009, 26 Pages.
Decision by German Patent Office in opposition proceedings for DE 100 80 167.6 (Feb. 17, 2009).
Submission by Alnylam Pharmaceuticals in the opposition proceedings of European Patent No. 1 214 945 (Nov. 20, 2008).
Submission by Alnylam Pharmaceuticals in the opposition proceedings of European Patent No. 1 144 623 (Nov. 7, 2008). (translation attached).
Submission by Alnylam Europe in opposition proceedings for European Patent No. 11 44 623 (Jun. 25, 2007).
Reply to notice of opposition by Alnylam Europe in the opposition proceedings of European Patent No. 1 214 945 (Dec. 28, 2006).
Submission by Alnylam Europe in opposition proceedings for European Patent No. 11 44 623 (Jun. 7, 2006).
Submission by Alnylam Europe in opposition proceedings for European Patent No. 11 44 623 (Apr. 21, 2006).
Submission by Alnylam Europe in opposition proceedings for European Patent No. 11 44 623 (Dec. 7, 2004).
Ambros, V., (2001 ), "Dicing Up RNAs", Science, 293:811-813.
Anderson, Nature, vol. 392, 25-30, 1998.
Anderson, "Human Gene Therapy," Nature, 392:25-30 (1998).
Armentano et al., "Expression of human factor IX in rabbit hepatocytes by retrovirus-mediated gene transfer: Potential for gene therapy of hemophilia B" Proc. Natl. Acad. Sci. USA 87:6141-6145 (1990).
Asanuma, H. et al., (1999), "Photoregulation der Bildung und Dissoziation eines DNA-Duplexes durch cis-trans-Isomerisierung einer Azobenzoleinheit", Angew. Chem., 111:2547-2549.
Notice of Opposition by AstraZeneca against European Patent No. 11 44 623 (May 28, 2003).
Submission by Atugen AG in opposition to European Patent No. 1 144 623 (Nov. 7, 2008).
Submission by Atugen in opposition proceedings for European Patent No. 11 44 623 (Apr. 21, 2006).
Notice of opposition by Atugen against European Patent No. 1 214 945 (Mar. 8, 2006).
Notice of Opposition by Atugen AG against European Patent No. 11 44 623 (May 28, 2003).
Response to Official Action filed for Australian Application No. 32713/00 (Oct. 19, 2004).
"Introduction of DNA into Mammalian Cells," Current Protocols in Molecular Biology, Supplement 48, Edited by Frederick M. Ausubel et al., John Wiley & Sons, Inc., on. 9.4.7-9.4.8 (1999).
Ausubel, F. et al. (1999) Supplement 48, pp. 9.4.7. to 9.4.8.
Auszug aus der online-Rolle des EPA, Excerpt from the European Patent Register for EP 1147204, Database last updated on Jun. 18, 2008, 4 Pages.
Notice of Opposition by Aventis against European Patent No. 11 44 623 (May 28, 2003).
Azhayeva, E. et al., ( 1997), "Inhibitory properties of double helix forming circular oligonucleotides", Nucl. Acids Res., 25:4954-4961.
Bahramian et al.; Molecular and Cellular Biology, vol. 19:274-283, 11Transcriptional and Posttranscriptional Silencing of Rodent a.1(1) Collagen by a Homologous Transcriptionally Self-Silenced Transgene Jan. 1999.

(56) References Cited

OTHER PUBLICATIONS

Barber et al., "Mutants of the RNA-Dependent Protein Kinase (PKR) Lacking Double-Stranded RNA Binding Domain I Can Act as Transdommant Inlubitors and Induce Malignant Transformation," Mol. Cell. Biol., 15(6):3138-3146 (1995).
Barlow et al., "Interferon synthesis in the early post-implantation mouse embryo" Differentiation 27:229-235 (1984).
Barwkar, D.A. et al.; Proc. Natl. Acad. Sci USA, vol. 95: 11047-11052, Sep. 1998, Chemistry, Biochemistrv.
Basbaum et al., "Focalized proteolysis: spatial and temporal regulation of extra cellular matrix degradation at the cell surface" Curr. Opin. Cell Biol. 8:731-738 (1996).
Bass, B.L., (2000), "Double-Stranded RNA as a Template for Gene Silencing", Cell, 101:235-238.
Baulcombe, D.C., et al., "Mechanisms of Pathogen-Derived Resistance to Viruses in Transgenic Plants," The Plant Cell (1996), 8: 1833-1844.
Baxevanis, A., "The Molecular Biology Database Collection: 2003 udpate," Nucleic Acids Research, 2003, pp. 1-12, vol. 31, No. 1.
Beck, "Unknotting the Complexities of Multidrug Resistance: The Involvement of DNA Topoisomerases in Drug Action and Resistance" J. Natl. Cancer Inst 81:1683-1685 (1989).
Beigelman, L., et al., "Synthesis of 2'-modified nucleotides and their incorporation into hammerhead ribozymes," Nucleic Acids Research, 1995, pp. 4434-4442, vol. 23, No. 21.
Berkner et al, "Development of Adenovirus Vectors for the Expression of Heterologous Genes" Bio Techniques 6 (7):616-629 (1998).
Bernstein, E., et al., "Role for a bidentate ribonuclease in the initation step of RNA interference," Nature, Jan. 18, 2001, pp. 363-366, vol. 409.
Bhan et al., Nucleic Acid Research, 1997; vol. 25; p. 3310.
Billy, et al. (2001) PNAS 98(25): 14428-33.
Biotechnology Applied Biochemistry vol. 29, Part 1, Feb. 1999, which shows Braun, H., et al., "Oligonucleotide and plasmid DNA packaging into polyoma VPI virus-like particles expressed in *Escherichia coli*," as first published on the internet Dec. 22, 1998.
Birkedal-Hansen et al, "Matrix Metalloproteinases: A Review" Grit Rev Oral Biol. Med 4:197-250 (1993).
Boese et al., "Mechanistic Insights Aid Computational Short Interfering RNA Design" Methods in Enzymology 392:73-95, 2005.
Boreckv et al. (1981-82) Tex Rep Biol Med 41:575-81 Abstract Only. Decision of Board of Appeal in Opposition for EP 114 46 23 (Mar. 29, 2009) (translation attached).
Boyd, "Invasion and metastasis" Cancer Metastasis Rev. 15:77-89 (1996).
Braasch et al, "Locked nucleic acid (LNA): fine-tuning the recognition of DNA and RNA" Chem. Biol. 8:1-7 (2001).
Braich et al., "Regiospecitic Solid-Phase Synthesis of Branched Oligonucleotides. Effect of Vicinal 2',5'-(or 2',3'-) and 3',5'-Phosphodiester Linkages on the Formation of Hairpin DNA," Bioconjug. Chem., 8:370-377 (1997).
Branch, "A good antisense molecule is hard to find," TIBS, 23:45-50 (1998).
Braun, H., et al., "Oligonucleotide and plasmid DNA packaging into polyoma VPI virus-like particles expressed in *Escherichia coli*," Biotechnol. Appl. Biochem, 1999, pp. 31-43.
Bremlicke et al., "RNA editing," FEMS Microbiology Reviews, 23:297-316 (1999).
Brinckerhoff et al, "Matrix metalloproteinases: a tail of a frog that became a prince" Nature Reviews 3:207-214 (2002).
Bruenig, "Plant Gene Silencing Regularized" Proc. Natl Acad Science 95:13349-13351, 1998.
Bucchini et al., "Pancreatic Expression of Human Insulin Gene in Transgenic Mice" PNAS USA 83:2511-2515 (1986).
Bumcrot, D., et al., "RNAi therapeutics: a potential new class of pharmaceutical drugs," Nature Chemical Biology (2006), 2(12): 711-719.
Burke et al., "Appearance of Interferon Inducibility and Sensitivity during Differentiation of Murine Teratocarcinoma Cells in Vitro" Cell 13:243-248 (1978).

Byrom et al., "Inducing RNAi with siRNA Cocktails Generated by RNase III," TechNotes 10(1), Ambion, http://www.ambion.com/techlib/tn/101/4.html (2004).
Cameron et al., "Inhibition of Gene Expression by a Short Sense Fragment" Nucleic Acids Research, 19:469-475, 1991.
Cameron, F.H., et al., "Specific gene suppression by engineered ribozymes in monkey cells," Proc. Natl. Acad. Sci., Biochemistry, Dec. 1989, pp. 9139-9143, vol. 86.
Caplen, "RNAi as a Gene Therapy Approach" Expert. Opin. Biol. Ther. 3:575-586, 2003.
Caplen, N.J., (2002), "A new approach to the inhibition of gene expression", TRENDS in Biotechnology, 20(2):49-51.
Caplen, N.J. et al., (2001), "Specific inhibition of gene expression by small double-stranded RNAs in invertebrate and vertebrate systems", Proc. Natl. Acad. Sci. USA, 98(17):9742-9747.
Caplen et al., "dsRNA-Mediated Gene Silencing in Cultured *Drosophila* Cells: a Tissue Culture Model for the Analysis of RNA Interference" Gene 252:95-105, 2000.
Castelli, J. et al., (998), "The 2-SA system in viral infection and apoptosis", Biomed. Pharmacother., 52:386-390.
Chao et al, "BCL-2 Family: Regulators of Cell Death" Annu. Rev. Immunol. 16:395-419 (1998).
Check, "RNAi to the rescue?" Nature 425:10-12, 2003.
Chen, M., et al., "A universal plasmid library encoding all permutations of small interfering RNA," PNAS, Feb. 15, 2005, pp. 2356-2361, vol. 102, No. 7.
Chen et al, "Gene therapy for brain tumors: regression of experimental gliomas by adenovirus-mediated gene transfer in vivo" Proc. Natl. Acad. Sci. USA 91:3054-3057 (1994).
Chien et al., "Novel cationic cardiolipin analogue-based. liposome for efficient DNA and small interfering RNA delivery in vitro and in vivo," Cancer Gene Therapy, pp. 1-8 (2004).
Childs et al., "The MDR Superfamily of Genes and Its Biological Implications" Imp. Adv. Oncol. 21-36 (1994).
Chowdhury et al, "Long-Term Improvement of Hypercholesterolemia After Ex Vivo Gene Therapy in LDLR-Deficient Rabbits" Science 254:1802-1805 (1991).
Chu, C-Y., et al., "Potent RNAi by short RNA triggers," RNA, Report, 2008, pp. 1714-1719, vol. 14.
Cioca et al., "RNA interference is a functional pathway with therapeutic potential in human myeloid leukemia cell lines" Cancer Gene Therapy 10:125-133 (2003).
Cobaleda, C. et al., (2000), "In vivo inhibition by a site-specific catalytic RNA subunit of Rnase P designed against the BCR-ABL oncogenic products: a novel approach for cancer treatment", Blood, 95(3):731-737.
Clemens MJ: PKR—a protein kinase regulated by double-stranded RNA. Int J Biochem Cell Biol 1997, 29(7):945-949.
Coburn et al., "siRNAs: a new wave of RNA-based therapeutics" Jour. Antimicrobial Chemotherapy 51:753-756, 2003.
Cole et al., "Overexpression of a Transporter Gene in a Multidrug-Resistant Human Lung Cancer Cell Line" Science 258:1650-1654 (1992).
Communication of Technical Board of Appeal in opposition to European Patent No. 1 144 623 (Sep. 22, 2008). (translation attached).
Cone et al., "High-efficiency gene transfer into mammalian cells: Generation of helper-free recombinant retrovirus with broad mammalian host range" Proc. Natl. Acad. Sci. USA 81:6349-6353 (1984).
Cook, "Medicinal chemistry of antisense oligonucleotides—future opportunities" Anti-Cancer Drug Design 6:585-607 (1991).
Corey, D.R., "Chemical modification: the key to clinical application of RNA interference?" The Journal of Clinical Investigation (2007), 117(12): 3615-3622.
Cornetia et al., "Safety Issues Related to Retroviral-Mediated Gene Transfer in Humans" Human Gene Therapy 2(1):5-14 (1991).
Cotten et al., "Ribozyme Mediated Destruction of RNA in vivo" EMBO J. 8:3861-3866, 1989.
Couture et al., "Anti-gene therapy: the use of ribozymes to inhibit gene function: Trends in Genetics," 12:510-515 (1996).
Couzin, "Small RNAs Make Big Splash," Science, 298:2296-2297 (2002).

(56) References Cited

OTHER PUBLICATIONS

Crooke, "Basic Principles of Antisense Therapeutics" Antisense Research and Application, Chapter 1, Springer-Verlag, NewYork, 1998.
Crooke et al., "Pharmacokinetic Properties of Several Novel Oligonucleotide Analogs in Mice" J. Pharmacol. Exp. Ther. 277:923-937 (1996).
Crooke, S., et al., "Antisense Research and Applications," Chapters 16 and 18, 1993, CRC Press, Boca Raton, 21 pages.
Current version of Curriculum Vitae of David M. Stalker, 2010, 13 pages.
Czauderna, F., Fechtner, M., Dames, S., Augun, H., Klippel, A., Pronk, G.J., Giese, K., Kaufmann, J., "Structural variations and stabilizing modifications of synthetic siRNAs in mammalian cells," Nucleic Acids Research, 2003, vol. 31, No. 11, rm. 2705-2716.
Czauderna et al., "Structural variations and stabilizing modifications of synthetic siRN As in mammalian cells." Nucleic Acids Res., 31(11):1-12 (2003).
Dai et al., "Gene therapy via primary myoblasts: Long-term expression of factor IX protein following transplantation in vivo" Proc. Natl. Acad. Sci. USA 89:10892-10895 (1992).
Damha, M. et al., "Chapter 5: Oligoribonucleotide synthesis: the silyl-phosphoramidite method," Methods in Molecular Biology 20, Edited by Sudhir Agrawal, Humana Press, NJ: 81-114 {{1993).
Danos et al., "Safe and efficient generation of recombinant retroviruses with amphotropic and ecotropic host ranges" Proc. Natl. Acad. Sci. USA 85:6460-6464 (1988).
D'Ari, "Cycle-regulated genes and cell cycle regulation" Bioassays 23:563-565 (2001).
de Fougerolles et al. Methods in Enzymology 2005, vol. 392, pp. 278-296.
Dean, N.M., et al., "Identification and Characterization of Second-Generation Antisense Oligonucleotides," Antisense & Nucleic Acid Drug Development (1997), 7: 229-233.
Decision in opposition proceedings for European Patent No. 11 44 623 (Mar. 30, 2009). (translation attached).
Decision Revoking Patent and Grounds for Decision in Opposition proceedings for EP 1214945 (Mar. 31, 2009).
Delgado et al., "The Uses and Properties of PEG-Linked Proteins" Grit Rev. Therap. Drug Carrier Sys. 9:249-304 (1992).
Dellweg et al., ed., :Römpp Lexikon Biotechnologies, p. 354 and p. 673 (1992) (in German).
Diagramm zur Illustrierung des Gegenstands des angegriffenen Patents.
Diagramm zur Illustrierung der Offenbarung van D5.
Diagramm zur Illustrierung der Offenbarung van D13.
Docherty et al., "Nutrient regulation of insulin gene expression" FAS EB J. 8:20-27 (1994).
Doench, J.G. et al., (2003), "siRNAs can function as miRNAs", Genes &Development, 17:438-442.
Dolinnaya, N.G. et al., "Oligonucleotide circularization by template-directed chemical ligation," Nucleic Acids Research, 21:5403-5407 (1993).
Donzé, O. et al., (2002), "RNA interference in mammalian cells using siRNAs synthesized with T7 RNA Polvmerase", Nucleic Acids Research, 30(10):e46(4pages.
Downward, J. et al., (1990), "Identification of a nucleotide exchange-promoting activity for p21$^{ras}$", Proc. Natl. Acad. Sci. USA", 87:5998-6002.
Dropulic, B., et al., "Functional Characterization of a U5 Ribozyme: Intracellular Suppression of Human Immunodeficiency Virus Type 1 Expression," Journal of Virology, Mar. 1992, pp. 1432-1441, vol. 66, No. 3.
Interlocutory Decision and Druckexemplar in opposition proceedings for European Patent No. 11 44 623 (Sep. 25, 2006).
Eder et al., "Monitoring of BCR-ABL expression using real-time RT-PCR in CML after bone marrow or peripheral blood stem cell transplantation" Leukemia 13:1383-1389 (1999).
Eglitis et al., "Gene Expression in Mice After High Efficiency Retroviral-Mediated Gene Transfer" Science 230:1395-1398 (1985).

Elbashir et al., "Analysis of gene function in somatic mammalian cells using small interfering RNAs," Methods, 26:199-213 (2002).
Elbashir, et al. (2001) Nature 411 :494-498.
Elbashir, S.M., Martinez, J., Patkaniowska, A., Lendeckel, W., Tuschl, T., "Functional anatomy of siRNAs for mediating efficient RNAi in *Drosophila melanogaster* embryo lysate," The EMBO Journal, vol. 20, No. 23, pp. 6877-6888, 2001.
Elbashir, S.M. et al., (2001), "RNA interference is mediated by 21- and 22-nucleotide RNAs", Genes & Development, 15:188-200.
Elbashir, S.M. et al., (2001), "Functional anatomy of siRNAs for mediating efficient RNAi in *Drosophila melanogaster* embryo lysate", The EMBO Journal, 20(23):6877-6888.
Eriksson et al., "Establishment and characterization of mouse stain (TLL) that spontaneously develops T-cell lymphomas/leukemia" Exp. Hematol. 27:682-688 (1999).
Expert-Bezancon, A. et al., "Precise localization of several covalent RNA-RNA cross-link in *Escherichia coli* 16S RNA," European Journal of Biochemistry, 136:267-274 (1983).
Fallert-Müller, ed., Encyclopedia of Biochemistry, vol. J-Z, pp. 448-449 (2000) (in German).
Fakler, B., et al., "Short Antisense Oligonucleotide-mediated Inhibition Is Strongly Dependent on Oligo Length and Concentration but Almost Independent of Location of the Target Sequence," The Journal of Biological Chemistry, Jun. 10, 1994, pp. 16187-16194, vol. 269, No. 23.
Fan et al., "Reversal of Multidrug Resistance in Cancer", ed. Kellen, CRC, Boca Raton, FL, pp. 93-125.
Ferry et al., "Retroviral-mediated gene transfer into hepatocytes in vivo" Proc. Natl. Acad. Sci. USA 88:8377-8381 (1991).
Fire, A., et al., 1991, Production of Antisense RNA leads to effective and specific inhibition of gene expression in *C. elegans* muscle, Development 113: 503-514.
Fire, 9/99, RNA-triggered gene silencing, Trends Genet, 15: 358-363.
Fire, A., "Gene Silencing By Double Stranded RNA," Nobel Lecture, Dec. 8, 2006, pp. 198-233.
Fire et al., "RNA Interferences—gene silencing by double-stranded RNA" The Nobel Prize in Physiology or Medicine, press release, 2006.
Fire, A. et al., (1998), "Potent and specific genetic interference by double-stranded RNA in *Caenorhabditis ele!lans*", Nature, 391:806-811.
Fire, A. et al., "Specific interference by ingested dsRNA," Nature, 395:854 (1998).
Forstova, J. et al., "Polyoma Virus Pseudocapsids as Efficient Carriers of Heterologous DNA into Mammalian Cells," Human Gene Therapy (1995), 6: 297-306.
Fotedar et al., "Apoptosis and the cell cycle" Prog. Cell Cycle Res. 2:147-163 (1996).
Gait, M., "Chapter 16: Oligoribonucleotides," Antisense Research and Applications, Edited by Stanley Crooke and Bernard Lebleu, CRC Press, 289-302 (1993).
Gao H., et al., "Circularization of oligonucleotides by disulfide bridge formation," Nucleic Acids Research, 23:2025-2029 (1995).
Gao, H., et al., "Stabilization of double-stranded oligonucleotides using backbone-linked disulfide bridges," Nucleic Acids Research, 1995, pp. 285-292, vol. 23, No. 2.
Grarnier, L. et al., "Incorporation of Pseudorabies Virus gD into Human Immunodeficiency Virus Type 1 Gag Particles Produced in Baculovirus-Infected Cells," Journal of Virology (1995) 69(7): 4060-4068.
Gassmann et al., "Maintenance of an extrachromosomal plasmid vector in mouse embryonic stem cells" PNAS USA 92:1292-1296 (1995).
Letter to the International Examining Authority from Gassner & Partner in the prosecution of PCT/DE00/00244 (WO 00/44895), 5 pages (Mar. 28, 2001) (in German).
Gautschi, O. et al., (200 I ), "Activity of a Novel bcl-2/bcl-xL-Bispecific Antisense Oligonucleotide Against Tumors of Diverse Histologic Origins", Journal of the National Cancer Institute, 93(6):463-471.

(56) References Cited

OTHER PUBLICATIONS

GenBank Accession No. U55763, "Cloning vector pEGFP-C1, complete sequence, enhanced green fluorescent protein (egfp) and neomycin phosphotransferase genes" Jun. 15, 1996.
GenBank Accession No. M13995, "Human B-cell leukemia/lymphoma 2 (bcl-2) proto-oncogene mRNA encoding bcl-2-beta protein" Oct. 31, 1994.
GenBank Accession No. M13994, "Human B-cell leukemia/lymphoma 2 (bcl-2) proto-oncogene mRNA encoding bcl-2-beta protein" Oct. 31, 1994.
Gewirtz, A., et al., "Nucleic Acid Therapeutics: State of the Art and Future Prospects," Blood, Aug. 1, 1998, pp. 712-736, vol. 92, No. 3.
Gibbs, J.B. et al., (1988), "Purification of ras GTPase activating protein from bovine brain", Proc. Natl. Acad Sci. USA, 85:5026-5030.
Gillock, E.T. et al., "Polyomavirus Major Capsid Protein VP1 is Capable of Packaging Cellular DNA When Expressed in the Baculovius System," Journal of Virology (1997),71(4): 2857-2865.
Graessman et al., "Inhibition of SV40 Gene Expression by Microinjected Small Antisense RNA and DNA Molecules" Nucleic Acids Research 19:53-59, 1991.
Graham, "Mapping Transgene Activity in Plants Using Visible Phenotypes" Australian Society for Biochemistry and 4 Molecular Biology Incorporated and Australian Society of Plant Physiologists Incorporated, vol. 28, Abstract D SYM-18-06 (1996).
Grasby, JA et al.; Biochemistry 1995 Mar 28; 3402);4068-76.
Green et al., "Antisense Oligonucleotides: An evolving technology for the modulation of gene expression in human disease" J. Am. Coll. Surg. 191:93-105, 2000.
Grierson et al., "Does Co-Suppression of Sense Genes in Transgenic Plants Involve Antisense RNA?" Trends in Biotechnology 9:122-123, 1991.
Griffey, RH et al.; J Med Chem Dec. 20, 1996; 39(26);5100-9.
Notice of Opposition by Dr. Martin Grund against European Patent No. 11 44 623 (May 28, 2003).
Gryaznov et al., "Template controlled coupling and recombination of oligonucleotide blocks containing thiophosphoryl groups," Nucleic Acids Res., 21(6):1403-1408 (1993).
Guang et al., "An Argonaute Transports siRNAs from the Cytoplasm to the Nucleus" Science 321:537-541, 2008.
Guo et al., "Par-1 a Gene Required for Establishing Polarity in *C. elegans* Embryos, Encodes a Putative Ser/Thr Kinase That is Asymmetrically Distributed" Cell 81:611-620, 1995.
Ha, I et al.; Genes Dev Dec. 1, 1996;10(23);3041-50.
Hamada M. et al., "Effects of RNA Interference in Gene Expression (RNAi) in Cultured Mammalian Cells of Mismatches and the Introduction of Chemical Modifications at the 3'-Ends of siRNAs," Antisense and Nucleic Acid Drug Development, 2002, vol. 12, pp. 301-309.
Hamilton et al.; Science, vol. 286:950-951, A Species of Small Antisense RNA in Posttranscriptional Gene Silencing in Plants (Oct. 29, 1999).
Hamm et al., "Incorporation of 2'-Deoxy-2'mercaptocytidine into Oligonucleotides via Phosphoramidite Chemistry" J. Org. Chem. 62:3415-3420 (1997).
Hammond, S.M. et al., (2000), "An RNA-directed nuclease mediates post-transcriptional gene silencing in *Drosophila* cells", Nature, 404:293-296.
Hanahan et al., "The Hallmarks of Cancer" Cell 100:57-70 (2000).
Harada et al., "Absence of the Type I IFN System in EC Cells: Transcriptional Activator (IRF-1) and Repressor (IRF-2) Genes Are Developmentally Regulated" Cell 83:303-312 (1990).
Harborth, J. et al., (2001 ), "Identification of essential genes in cultured mammalian cells using small interfering RNAs", Journal of Cell Science, 114(24):4557-4565.
Harris et al., "The Eu-myc Transgenic Mouse A Model for High-incidence Spontaneous Lymphoma and Leukemia of Early B Cells" J. Exp. Med. 167(2):353-371 (1988).

Harfe et al. 1998, Analysis of a *Caenorhabditis elegans* twist homolog identifies conserved and divergent aspects of mesodermal patterning, Genes and Development, 12: 2623-2635.
Hedges, "The Origin and Evolution of Model Organisms," Nature Reviews, 3:838-849 (2002).
Hendry, P., et al., "Redesigned and chemically-modified hammerhead ribozymes with improved activity and serum stability," BMC Chemical Biology, Dec. 9, 2004, pp. 1-11, vol. 4, No. 1.
Hoke, GD et al.; Nucleic Acids Res Oct. 25, 1991; 19(20):5743-8.
Hom, T et al.; Nucleic Acids Research, 1997, vol. 25, No. 23 : 4842-4849.
Nolen, T. et al., (2002), "Positional effects of short interfering RNAs targeting the human coagulation trigger Tissue Factor", Nucleic Acids Research, 30(8): 1757-1766.
Horn. T et al.; Nucleic Acids Research, 1997 vol. 25, No. 23 : 4842-4849.
Hornung et al., "Sequence-specific potent induction of IFN-a by short interfering RNA in plasmacytoid dendritic cells throm!h TLR7," Nature Medicine, 11(3):263-270 (2005).
Hsu et al., "Immunogenicity of Recombinant Adenovirus-Respiratory Syncytial Virus Vaccines with Adenovirus Types 4, 5, and 7 Vectors in Dogs and a Chimpanzee" J. Infectious Disease 166:769-775 (1992).
Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma" Cancer Res., 65(19):8984-8992 (2005).
Huber et al., "Retroviral-mediated gene therapy for the treatment of hepatocellular carcinoma: An innovative approach for cancer therapy" Proc. Natl. Acad. Sci. USA 88:8039-8043 (1991).
Hung, C., et al., "A novel siRNA validation system for functional screening and identification of effective RNAi probes in mammalian cells," Biochemical and Biophysical Research Communications, 2006, pp. 707-720, vol. 346.
Hunter, Jun. 17, 1999, A tau.ch of elegance with RNAi, Curr Biolo. 9:R440-R442.
Hunter et al., "The characteristics of inhibition of protein synthesis by double stranded ribonucleic acid in reticulocyte lysates," J. Biol. Chem., 250(2):409-417 (1975).
Hwu et al., "Functional and Molecular Characterization of Tumor-Infiltrating Lymphocytes Transduced with Tumor Necrosis Factor-alpha cDNA for the Gene Therapy of Cancer in Humans" J. Immunol. 150:4104-4115 (1993).
"InBase, The Intein Database: The Intein Registry—Inteins Sorted by Species," http://tools.neb.com/inbase/list.phg (database undated on May 22, 2006).
Inouye, M., Antisense RNA: Its functions and applications in gene regulation—a review Gene, 1988, pp. 25-34, vol. 72.
International Preliminary Examination Report from PCT/DE00/00244.
Notice of Opposition by Isis Pharmaceuticals against European Patent No. 11 44 623 (May 28, 2003).
Ichim, T., et al., "RNA Interference: A Potent Tool for Gene-Specific Therapeutics," American Journal of Transplantation, 2004, vol. 4, pp. 1227-1236.
Iwase, R et al.; Nucleic Acids Svmp Ser 1997 (37);203-4.
Izant et al., "Constitutive and Conditional Suppression of Exogenous and Endogenous Genes by Anti-Sense RNA" Science 229:345-352, 1985.
Jackson, A. L. et al., "Widespread siRNA "off-target" transcript silencing mediated by seed region sequence complementarity," RNA Journal, 12(7): 1179-1187 (2007).
Jacobs, B.L., and Langland, J.O., 1996, When two stands are better than one: The mediators and modulators of the cellular responses to double-stranded RNA. Virology 219: 339-349.
James et al., "The Therapeutic Potential of Ribozymes" Blood 91:371-382 (1998).
Jaschke, et al., "Synthesis and analytical characterization of RNA polyethylene glycol conjugates," Nucleosides & Nucleotides, 15:1519-1529 (1996).
Jeffrey, I., et al., "Nuclear Localization of the Interferon-Inducible Protein Kinase PKR in Human Cells and Transfected Mouse Cells," Experimental Cell Research, 1995, pp. 17-27, vol. 218, No. 1.

(56) References Cited

OTHER PUBLICATIONS

Jen et al., "Suppression of Gene Expression by Targeted Disruption of Messenger RNA: Available Options and Current Strategies" Stem Cells 18:307-319, 2000.
Jennings et al., "Inhibition of SV40 Replicon Function by Engineered Antisense RNA Transcribed by RNA Polymerase III" EMBO Journal 6:3043-3047, 1987.
Notice of Opposition by Janssen Pharmaceuticals against European Patent No. 11 44 623 (May 28, 2003).
Jiang, A., et al., "In vivo cell type-specific gene delivery with retroviral vectors that display single chain antibodies," Gene Therapy, 1999, pp. 1982-1987, vol. 6.
Jorgensen et al., "Silencing of Plant Genes by Homologous Transgenes" AgBiotech News and Information 4:265-273, 1992.
Judge A.O., et al., "Design of Noninflammatory Synthetic siRNA Mediating Potent Gene Silencing in Vivo," Molecular Therapy (2006), 13(3): 494-505.
Judge et al., "Sequence-dependent stimulation of the mammalian innate immune response by synthetic siRNA," Nat. Biotechnol. pp. 1-6 (2005) (8 pages of supplementary content included).
Kabanov et al., "A new class of antivirals: antisense oligonucleotides combined with a hydrophobic substituent effectively inhibit influenza virus reproduction and synthesis of virus-specific proteins in MOCK cells" FEBS Lett. 259 (2):327-330 (1990).
Kamio et al., "Nucleotide Sequence of an Incompatibility Region of Mini-Rts1 That Contains Five Direct Repeats" Journal of Bacteriology 155:1185-1191, 1983.
Kaufman, R.J., et al., "Double-stranded RNA-activated protein kinase mediates virus-induced apoptosis: A new role for an old actor," PNAS USA, 96:11693-11695 (1999).
Kay et al., "Hepatic Gene Therapy: Persistent Expression of Human alpha1-Antitrypsin in Mice after Direct Gene Delivery in Vivo" Human Gene Therapy 3:641-647 (1992).
Kelly, J. "Superagonist Trial Hit by Cytokine Storm," Muscoskeletal Report, Aug. 17, 2006, 3 pages.
Kennerdell et al., "Use of dsRNA-Mediated Genetic Interference to Demonstrate that frizzled and frizzled 2 Act in the Wingless Pathway," Cell, 95:1017-1026 (1998) (Abstract).
Kennerdell et al.; Cell, vol. 95, S. 1017-1026; "Use of dsRNA-Mediated Genetic Interference to Demonstrate that frizzled and frizzled 2 Act in the Wingless Pathway" Dec. 23, 1998.
Kim et al., "Stable Reduction of Thymidine Kinase Activity in Cells Expressing High Levels of Anti-Sense RNA" Cell 42:129-138, 1985.
Kitabwalla et al., "RNA-Interference. A New Weapon Against HIV and Beyond," N. Engl. J. Med., 347(17):1364-1367 (2002).
Klemens, et al. (1999), The 2 A Structure of helix 6 of the human signal recognition particle RNA., Structure 7(11): 1345-1352. (Abstract).
Koshkin et al., "LNA (Locked Nucleic Acids) Synthesis of the Adenine, Cytosine, Guanine, 5-Mehtylcytosine, Thymine and Uracil Biclonucleoside Monomers, Oligomerisation, and Unprecedented Nucleic Acid Recognition," Tetrahedron 54:3507-3630 (1998).
Kovalchuk et al., "Burkitt Lymphoma in the Mouse" J. Exp. Med. 192:1183-1190 (2000).
Krieger et al., "The Flavr Savr Tomato, an Early Example of RNA/ Technology" HortScience 43:962-964, 2008.
Krepela, "Cysteine proteinases in tumor cell growth and apoptosis" Neoplasma 48:332-349 (2001).
Kreutzer et al (1999) Gesellschaft fur Biochemie und Molekularbiologie S169 (Abstract).
Kreutzer, R., Limmer, S., Application No. 199 03 713.2, "Medication for Inhibiting Expression of a Defined Gene, "English translation of priority document for PCT/DE 00/00244, German Patent and Trademark Office, May 11, 2000.
Kreutzer, R., Limmer, S., Application No. 199 56 568.6, "Method and Medication for Inhibiting the Expression of a Defined Gene," English translation of priority document for PCT/DE 00/00244, German Patent and Trademark Office, May 11, 2000.

Kreutzer et al., Specific Inhibition of Viral Gene Expression by Double-Stranded RNA in vitro. Annual Fall Meeting of the GBH, Sep. 5, 1999, Abstract Nr. 328.
Kreutzer et al., Specific inhibition of viral gene expression by double-stranded RNA in vitro. Sep. 8, 1999. Annual Fall Meeting of GBH, Poster 328.
Madhur Kumar et al. "Antisense RNA: Function and Fate of Duplex RNA in Cells of Higher Eukaryotes" Microbiology and Molecular Biology Reviews, vol. 62, Dec. 1998, pp. 1415-1434.
Kuss, B., et al., "Antisense—time to shoot the messenger," Annals of Oncology, 1999, pp. 495-503, vol. 10.
Lamond, A., et al., "Antisense oligonucleotides made of 2'-0-alkyl RNA: their properties and applications in RNA biochemistry," FEBS Letters (1993), 325(1-2): 123-127.
Lederer & Keller; English Version of German Opposition, filed by Pfizer Inc. on Jun. 19, 2008, in opposition to German Patent DE 100 66 235.8 (translation attached).
Lee et al., "The *C. elegans* Heterochronic Gene lin-4 Encodes Small RNAs with Antisense Complementarity to lin-14," Cell, 75:843-854 (1993).
Lee, et al.; Cell, vol. 88; S. 637-646; Mar. 7, 1997; The Cold Shock Domain Protein LIN-28 Controls Developmental Timing in *C. elegans* and Is Regulated by the lin-4 RNA.
Lesnik, E., et al., "Oligodeoxynucleotides Containing 2'-0-Modified Adenosine: Sythesis and Effects on Stability of DNA: RNA Duplexes," Biochemistry, 1993, pp. 7832-7838, vol. 32.
Letsinger et al., "Cholesteryl-conjugated oligonucleotides: Synthesis, properties, and activity as inhibitors of replication of human immunodeficiency virus in cell culture" PNAS USA 86:6553-6556 (1989).
Lewis, D.L. et al., (2002), "Efficient delivery of siRNA for inhibition of gene expression in postnatal mice", Nature Genetics, 32:107-108.
Li et al., Dev. Biology vol. 210, 1999, p. 238 abstract 346.
Lin et al.; Nature, vol. 402: 128-129, "Policing rogue genes" Nov. 11, 1999.
U.S. Appl. No. 60/117,335, Li et al. (filed Jan. 28, 1999).
Li et al., "Folate-Mediated Targeting of Antisense Oligodeoxynucleotides to Ovarian Cancer Cells" Pharm. Res. 15 (10):1540-1545 (1998).
Lipardi, C. et al., (2001), "RNAi as Random Degradative PCR: siRNA Primers Convert mRNA into dsRNAs that Are Degraded to Generate New siRNAs", Cell, 107:297-307.
Lipinski, et al. (1997) Adv. Drug Delivery Review 23:3-25.
Lipson, S.E., et al., "Psoralen cross-linking of ribosomal RNA," Methods in Enzymology, 164:330-341 (1988).
Liu, Z. R., et al., Detection of a novel ATP-dependent cross-linked protein at the 5' splice site-U1 small nuclear RNA duplex by methylene blue-mediated photo-cross-linking, Molecular Cell Biology, 18:6910-6920 (1998).
Livache et al., "Detection of HIV1 DNA in Biological Samples by an Homogenous Assay: Fluorescence Measurement of Double-Stranded RNA Synthesized from Amplified DNA" Analytical Biochemistry, 217:248-254, 1994.
Loke, S. L., et al., "Characterization of oligonucleotide transport into living cells," Proc. Natl. Acad. Sci., Biochemistry, May 1989, pp. 3474-3478, vol. 86.
Lopez-Fraga, M., et al., "RNA Interference-Based Therapeutics: New Strategies to Fight Infectious Disease," Infectious Disorders Drug Targets (2008), 8:262-273.
Lowy D.R. et al., (1993), "Function and Regulation of RAS", Annu. Rev. Biochem., 62:851-891.
Lubberts, E., et al., "Adenoviral Vector-Mediated Overexpression of IL-4 in the Knee Joint of Mice with Collagen-Induced Arthritis Prevents Cartilage Destruction," The Journal of Immunology, 1999, pp. 4546-4556.
Luo et al., "The Gene-Silencing Efficiency of siRNA is Strongly Dependent on the Local Structure of mRNA at the Targeted Region" Biochemical and Biophysical Research Communications, vol. 318(1):303-10 (2004).
Ma MY (1993) Biochem. 32(7):1751-8.
Maitra et al., "HIV-1 TAR RNA Has an Intrinsic Ability to Activate Interferon-Inducible Enzymes" Virology 204:823-827, 1994.
Majumdar, A et al.; Nat Genet Oct. 1998; 20(2):212-4.

(56) References Cited

OTHER PUBLICATIONS

Malone, R.W. et al., "Cationic liposome-mediated RNA transfection," Proc. Natl. Acad. Sci. USA (1989), 86:6077-6081.
Manche, L. et al., (1992), "Interactions between Double-Stranded RNA Regulators and the Protein Kinase DAI", Molecular and Cellular Biology, 12(11):5238-5248.
Manoharan, Oligonucleotide Conjugates as Potential Antisense Drugs with Improved Uptake, Biodistribution, Targeted Delivery and Mechanism of Action: Antisense and Nucleic Acid Drug Development 12:103-128 (2002).
Manoharan. Oligonucleotide Conjugates as Potential Antisense Drugs with Improved Uptake. Biodistribution, Targeted Delivery and Mechanism of Action: Antisense and Nucleic Acid Drug Development 12:103-128 (2002).
Manoharan et al, "Chemical Modifications to Improve Uptake and Bioavailability of Antisense Oligonucleotides" Ann. NY Acad. Sci. 660:306-309 (1992).
Manoharan et al, "Introduction of a Lipophilic Thioether Tether in the Minor Groove of Nucleic Acids for Antisense Applications" Bioorg. Med. Chem. Lett. 3(12):2765-2770 (1993).
Manoharan et al, "Cholic Acid-Oligonucleotide Conjugates for Antisense Applications" Bioorg. Med. Chem. Lett. 4(8):1053-1060 (1994).
Manoharan et al, "Oligo Acid-Oligonucleotide Conjugates Alteration of the Pharmacokinetic Properties of Antisense Agents" Nucleosides & Nucleotides 14:969-973 (1995).
Manoharan et al, "Lipidic Nucleic Acids" Tetrahedron 36:3651-3654 (1995).
Manoharan, M., "RNA interference and chemically modified small interfering RNAs," Current Opinion in Chemical Biology (2004), 8: 570-579.
Martinez et al., "Single stranded antisense siRNAs guide target RNA cleavage in RNAi," Cell, 110:563-574 (2002).
Maru, "Molecular Biology of Chronic Myeloid Leukemia" Int J. Hematol. 73:308-322 (2001).
Marques et al., "A Structural Basis for Discriminating Between Self and Non-Self Double-Stranded RNAs in Mammalian Cells" Nature Biotechnology 24:559-65, 2006.
Marques et al., "Activation of the mammalian immune system by siRNAs," Nat. Biotechnol., 23(11):1399-1405 (2005).
Martinez et al., "Single-Stranded Antisense siRNAs Guide Target RNA Cleavage in RNAi." Cell, 110:563-574 (2002).
Matrisian, "Cancer biology: Extracellular proteinases in malignancy" Curr. Biol. 9(20):R776-778 (1999).
McCaffrey, A.P. et al., (2002), "RNA interference in adult mice", Nature, 418:38-39.
McCall, M., et al., "Minimized Hammerhead Ribozymes," Methods in Molecular Biology, 1997, pp. 151-159, vol. 74.
McManus et al., "Gene Silencing in Mammals by Small Interfering RNAs," Nat. Rev. Genet., 3:737-747 (2002).
Meister, "RNA Interference in the Nucleus" Science 321:496-497, 2008.
Mendelsohn et al, "The EGF receptor family as target for cancer therapy" Oncogene 19(56):6550-6565 (2000).
Micura, R. "Cyclic oligoribonucleotides (RNA) by solid-phase synthesis," Chem. Eur. J., 5:2077-2082 (1999).
Mignatti et al, "Biology and Biochemistry of proteinases in Tumor Invasion" Physiol. Rev. 73:161-195 (1993).
Milhaud et al., Journal of Interferon Research, 1991, vol. 11, 261-265.
Milligan et al., "Synthesis of Small RNAs Using T7 RNA Polymerase" Methods in Enzymology, 180:51-62, 1989.
Minks, M. A. et al., The Journal of Biological Chemistry (1979), vol. 254, pp. (20):10180-10183.
Mishra et al, "Improved leishmanicidal effect of phosphorotioate antisense oligonucleotides by LDL-mediated delivery" Biochem. Biophys. Acta. 1264:229-237 (1995).
Mizuno et al., "Regulation of Gene Expression by a Small RNA Transcript (micRNA) in *Escherichia coli* K-12)" Proc. Japan Acad. 59:335-338, 1983.

Misquitta, L. and Paterson, B.M., 1999, Targeted disruption of gene function in *Drosophila* by RNA interference (RNA-i): A role/or nautilus in embryonic somatic muscle formation, Proc. Natl. Aca.d. Sci. 96: 1451-1456.
Monia, B.P. et al., "Evaluation of 2'-Modified Oligonucleotides Containing 2'-Deoxy Gaps as Antisense Inhibitors of Gene Expression," The Journal of Biological Chemistry (1993), 268(19): 14514-14522.
Montgomery, M., and Fire, 1998, Analysis of a *Caenorhabditis elegans* twist homolog identifies conserved and divergent aspects of mesodermal patterning, Genes and Development, 12: 2623-2635.
Montgomery M.K., et al., 1998. RNA as a target of double-stranded RNA-mediated genetic interference in *Caenorhabditis elegan*, Proc. Natl. Acad. Sci. 95: 15502-15507.
Montgomery, et al., Jul. 1998, Double-stranded RNA as a mediator in sequence-specific genetic Silencing and co-suppression, TIG, vol. 14, No. 7, pp. 255-258.
Morita et al., "RNAi Provides a New Tool for Functional Analyses of Mammalian Genes", Proteins, Nucleic Acids and Enzymes, vol. 47, No. 14, 2002, pp. 1939-1945, with English Abstract.
Moss et al., "The Cold Shock Domain Protein LIN-28 Controls Developmental Timing in *C. elegans* and Is Regulated by the lin-4 RNA," Cell, 88:637-646 0997).
Muellauer et al, "Mutations in apoptosis genes: a pathogenetic factor for human disease" Mutat. Res. 488:211-231 (2001).
Muzyczka, "Use of Adena-Associated Virus as a General Transduction Vector for Mammalian Cells" Curr. Topics Micro. Immunol. 158:97-129 (1992).
Declaration of David Keith Myers filed in opposition proceedings for Australian Patent 778474 (Nov. 4, 2008).
Exhibit 1 of David Keith Myers Declaration filed in opposition proceedings for Australian Patent 778474 (Nov. 4, 2008).
Exhibit 2 of David Keith Myers Declaration filed in opposition proceedings for Australian Patent 778474 (Nov. 4, 2008).
Nakamura et al., "How Does RNase H recognize a DNA-RNA Hybrid?" Proc. Natl. Acad. Sci. 88:11535-11539 (1991).
Napoli et al., "Introduction of a chimeric Chalcone Synthase Gene into *Petunia* Results in Reversible Co-Suppression of Homologous Genes in trans" The Plant Cell 2:279-289, 1990.
Various, "Nature Insight: RNA interference," Nature, 431:337-378 (2004).
Neilsen et al. (1997) Chem. Comm. 825-826.
Ngo, H., et al., 1998, Double-stranded RNA induces mRNA degradation in *Trypanosoma brucei*, Proc. Natl. Acad. Sci. 95: 14687-14692.
Nielsen et al., "A novel class of conformationally restricted oligonucleotide analogues: synthesis of 2',3'-bridged monomers and RNA-selective hybridization." Chem. Commun., pp. 825-826 (1997).
Nikiforov, et al. (1992) Nucleic Acids Research 20(6):1209-1214.
Nishi, T., et al., "High-Efficiency in Vivo Gene Transfer Using Intraarterial Plasmid DNA Injection following in Vivo Electroporation 1," Cancer Research, Mar. 1, 1996, pp. 1050-1055, vol. 56.
Niu, G., et al., "Gene Therapy with Dominant-negative Stat3 Suppresses Growth of the Murine Melanoma 816 Tumor in Vivo1," Cancer Research, Oct. 15, 1999, pp. 5059-5063, vol. 59.
Normanno et al, "The role of EGF-Related Peptides in Tumor GroVvih" Front. Biosci. 6:D685-707 (2001).
Notice of Opposition by Novartis against European Patent No. 11 44 623 (May 28, 2003).
Novina et al., "The RNAi revolution" Nature 430:161-164, 2004.
Oates et al., "Too Much Interference: Injection of Double-Stranded RNA Has Non-Specific Effects in the Zebrafish Embryo" Developmental Biology 24:20-28, 2000.
Oberhauser et al, "Effective incorporation of 2'-O-methyl-oligoribonucleotides into liposomes and enhanced cell association through modification with thiocholesterol" Nucl. Acids Res. 20:533-538 (1992).
Obika et al, "Stability and structural features of the duplexes containing nucleoside analogues with a fixed N-type conformation, 2'-O,4'-C-methyleneribonucleosides" Tetrahedron 39:5401-5404 (1998).
Statutory Declaration by Martin Edward O'Brien of Spruson and Ferguson in the matter of Opposition to Australian Patent No. 778474, filed by Sirna Therapeutics, Inc. on Aug. 29, 2008.

(56) References Cited

OTHER PUBLICATIONS

Opalinska et al., "Nucleic Acid therapeutics: basic principles and recent applications" Nature Reviews 1:503-514, 2002.
Ouchi et al., "Synthesis and Antitumor Activity of Poly(Ethylene Glycol)s Linked to 5-Flurouracil via a Urethane or Urea Bond" Drug Design and Discovery 9:93-105 (1992).
Oxford Advanced Learner's Dictionary of Current English, p. 253.
Paddison, P.J. et al., (2002), "Short hairpin RNAs (shRNAs) induce sequence-specific silencing in mammalian cells", Genes & Development, 16:948-958.
U.S. Appl. No. 60/130,377, Pachuk. et al. (filed Apr. 21, 1999).
Pandolfi, "In vivo analysis of the molecular genetics of acute promyelocytic leukemia" Oncogene 20:5726-5735 (2001).
Minutes of the Oral Proceedings in opposition proceedings for European Patent No. 11 44 623 (Jun. 22, 2006).
Overview, http://arthritis-research.com/content/figures/ar1168-1.jpg, Jan. 12, 2010.
Parrish, S. et al., "Functional anatomy of a dsRNA trigger: differential requirement for the two trigger strands in RNA interference," Molecular Cell, 6:1077-1087 (2000).
Paroo et al., "Challenges for RNAi in vivo" Trends in Biotechnology 22:390-394, 2004.
Paul et al., "Effective expression of small interfering RNA in human cells" Nature Biotechnology 29:505-508, 2002.
PCT/GB00/04404 as filed (Nov. 19, 1999).
Pei et al., "On the Art of Identifying Effective and Specific siRNAs" Nature Methods 3: 670-676, 2006.
Parrish, S. et al, "Functional anatomy of a dsRNA trigger: differential requirement for the two trigger strands in RNA interference," Molecular Cell, 6:1077-1087 (2000).
Pegram et al., "Phase II Study of Receptor-Enhanced Chemosensitivity Using Recombinant Humanized Anti-p185$^{HER2/neu}$ Monoclonal Antibody Plus Cisplatin in Patients With HER2/neu-Overexpressing Metastatic Breast Cancer Refractory to Chemotherapy Treatment," J. Gin. Oncol., 16(8):2659-2671 (1998).
Pegram, MD et al.; J. Clin Oncol Aug. 1998; 16(8):2659-71.
Perler, "InBase: the Intein Database," Nucleic Acids Res., 30(1):383-384 (2002).
Notice of Opposition to European Patent EP 1550719 filed by Pfizer Limited, filed Sep. 23, 2009, 21 pages.
Petition by Pfizer Inc. in opposition proceedings for German Patent No. 10066235.8 (May 25, 2009).
Notice of Opposition by Pfizer against DE 100 80 167.6 (Jun. 19, 2008) (translation attached).
German Opposition, filed by Pfizer Inc. on Jun. 19, 2008, in opposition to German Patent DE 100 66 235.8.
Written Submission by Pfizer in Opposition proceedings for DE 100 80 167.6 (Feb. 27, 2009).
Notice of Opposition to German Application No. DE 100 66 235, filed by Pfizer Inc. on Jul. 9, 2008.
Notice of Opposition to German Application No. DE 100 66 235, filed by Sanofi Aventis Deutschland GmbH on Jul. 10, 2008.
Notice of Opposition by Sanofi Aventis against DE 100 80 167.6 (Jun. 16, 2008).
List of Documents in Oppositions to German Application No. DE 100 66 235, filed by Silence Therapeutics AG, Sanofi Aventis Deutschland GmbH, and Pfizer Inc.
Phillips et al, "The NZB Mouse as a Model for Chronic Lymphocytic Leukemia" Cancer Res. 52:437-443 (2000).
Phillips, M., "Antisense Inhibition and Adena-Associated Viral Vector Delivery for Reducing Hypertension," Hypertension, Journal of the American Heart Association, 1997, Paaes 177-187, vol. 29.
Pils, W. et al, "Flexible non-nucleotide linkers as loop replacements in short double helical RNAs," Nucleic Acids Research, 28(9): 1869-1963 (2000).
Response to Notice of Opposition filed against German Patent No. DE 01985833, filed by Max-Plank—Gesellschaft zur Forderuna der Wissenschaften e.V., Mar. 26, 2009, 4 pages.
Pollock et al, "Mouse models of acute promyelocytic leukemia" Curr. Opin. Hematol. 8:206-211 (2001).
Polushin et al, "Synthesis of Oligonucleotides Containing 2'-Azido- and 2'-Amino-2'-deoxyuridine Using Phosphotriester Chemistry" Tetrahedron 37:3227-3230 (1996).
Prakash et al., J. Med. Chem. 2005, pp. 4247-4253.
Psychremebel Klinisches Worterbuch, 259, neu bearbeitete Auflage.
Pschyrembel Klinisches Worterbuch, 259., neu bearbeitete Auflage, Pschyrembel Clinical Dictionary 259m, Revised Edition, 2002, 1 page, with English summary.
Response to patentee's Grounds of Appeal filed by Quark Biotech, Inc. for European Patent EP 1214945, filed Dec. 28, 2009, 12 pages.
Notice of opposition Quark Biotech against European Patent No. 1 214 945 (Mar. 7, 2006).
Pusch et al., "Nucleotide Sequence Homology Requirements of HIV-1 Specific Short Hairpin RNA" Nucleic Acids Research 31:6444-6449, 2003.
Randall, G. et al., (2003), "Clearance of replicating hepatitis C virus replicon RNAs in cell culture by small interfering RNAs", PNAS, 100(1):235-240.
Ravasio, "Selective Hydrogenations Promoted by Copper Catalysts. 1. Chemoselectivity, Regioselectivity, and Stereoselectivity in the Hydrogenation of 3-Substituted Steroids" J. Org. Chem. 56:4329-4333 (1991).
Ravinderjit et al., "Regiospecific Solid-Phase Synthesis of Branched Oligonucleotides. Effect of Vicinal 2',5'- (or 2',3'-) and 3',5'-Phosphodiester Linkages on the Formation of Hairpin DNA," Bioconjugate Chemistry, 8:370-377 (1997).
Reed, "Mechanisms of Apoptosis" Am. J. Pathol. 157:1415-1430 (2000).
Regalado, "Turning Off Genes Sheds New Light On How They Work," The Wall Street Journal, 4 pages (Aug. 6, 2002).
Rego et al., "Analysis of the Molecular Genetics of Acute Promyelocytic Leukemia in Mouse Models" Semin. in Hemet. 38:54-70 (2001).
Reynolds et al., "Rational siRNA design for RNA interference" Nature Biotechnology 22:326-330, 2004.
Robbins et al., "Sensing the danger in RNA," Nat. Med., 11(3):250-251 (2005).
Notice of Opposition to European Patent EP 1550719 filed by Sarah Elizabeth Rogues, filed Sep. 23, 2009, 24 pages.
Rosalind, C. L., et al., "The C. elegans Herochronic Gene lin-4 encodes small RNAs with antisense complementary to lin-14," Cell, 75:843-854 (1993).
Rosalind C. Lee, et al.; Cell, vol. 75, 843-854, Mar. 12, 1993; "The C.elegans Herochronic Gene lin-4 Encodes Small RNAs with Antisense Complementary to lin-14".
Rosenfeld et al., "Adenovirus-Mediated Transfer of a Recombinant a-Antitrypsin Gene to the Lung Epithelium in Vivo" Science 252:431-434 (1991).
Rosenfeld et al, "In Vivo Transfer to the Human Cystic Fibrosis Transmembrane Conductance Regulator Gene to the Airway Epithelium" Cell 68:143-155 (1992).
Rumney, S., et al., "Structural Optimization of Non-Nucleotide Loop Replacements for Duplex and Triplex DNAs," J. Am. Chem. Soc., 1995, pp. 5635-5646, vol. 117.
Saison-Behmoaras et al., "Short modified antisense oligonucleotides directed against Ha-ras point mutation induce selective cleavage of the mRNA and inhibit T24 cells proliferation" EMBO J. 10:111-118 (1991).
Grounds of Appeal filed by Appellant Sanofi-Aventis Deutsch land GmbH, on Oct. 26, 2010, against German Patent No. DE 10066235.8, 21 pages.
Notice of Opposition to European Patent EP 1550719 filed by Sanofi-Aventis Deutschland GmbH, filed Sep. 23, 2009, 46 pages.
Notice of Opposition to German Application No. DE 10066235, filed by Sanofi Aventis Deutschland GmbH on Jul. 10, 2008, 42 pages.
Petition by Sanofi-Aventis et al. in opposition proceedings for German Patent No. 10066235.8 (May 22, 2009).
Scheffer et al., "The drug resistance-related protein LRP is the human major vault protein" Nat. Med. 1:578-582 (1995).
Scherr et al., "Quantitative Determination of Lentiviral Vector Particle Numbers By Real-time PCR" Bio Techniques 31:520-526 (2001).

(56) References Cited

OTHER PUBLICATIONS

Schlingensiepen et al., Blackwell Science Ltd., vol. 6, 1997, "Antisense—From Technology to Therapy".
Schwarz et al., "Asymmetry in the assembly of the RNAi complex" Cell 115:199-208, 2003.
Schwarz et al., "Evidence that siRNAs Function as Guides, Not Primers, in the *Drosophila* and Human RNAi Pathways," Mol. Cell 10:537-548 (2002).
Secrist et al., Abstract 21, Program & Abstracts, Tenth International Roundtable, Nucleotides, Nucleotides and their Biological Applications, Park City, Utah, Sep. 16-20, 1992.
Sedlik, C. et al., "Recombinant parvovirus-like particles as an antigen carrier: A novel nonreplicative exogenous antigen to elicit protective antiviral cytotoxic T cells," Proc. Natl. Acad. Sci. USA (1997) 94:7503-7508.
Sen, G., et al., "A Brief History of RNAi: The Silence of the Genes," FASEB J., vol. 20, pp. 1293-1299, 2006.
Seow, Y., et al., "Biological Gene Delivery Vehicles: Beyond Viral Vectors," Molecular Therapy (2009), 17(5): 767-777.
Seydoux, G., et al., "Repression of gene expression in the embryonic germ lineage of *C.elegans*," Nature 382:713-716 (1996).
Sharp, "RNA Interference—2001," Genes and Development 15:585-490, 2001.
Shannon et al., "Modeling myeloid leukemia tumors suppressor gene inactivation in the mouse" Semin. Cancer Biol. 11:191-199 (2001).
Sharp et al., "RNAi and double-strand RNA," Genes Dev., 13:139-141 (1999).
Shea et al., "Synthesis, hybridization properties and antiviral activity of lipid-oligodeoxynucleotide conjugates" Nucl. Acids Res. 18:3777-3783 (1990).
Shi et al., "A CBP/p300 homolog specifics multiple differentiation pathways in *Caenorhabditis elegans*," Genes Dev., 12:943-955 (1998).
Shibahara, S., et al., "Inhibition of human immunodeficiency virus (HIV-1) replication by synthetic oligo-RNA derivatives," Nucleic Acids Research, 1989, pp. 239-252, vol. 17, No. 1.
Sinha, "Large-scale Synthesis. Approaches to Large-scale Synthesis of Oligodeoxynucleotides and their Analogs," Antisense—From Technology to Therapy. Volume 6, Edited by Reimar Schlingensienen et al., pp. 29-58 (1997).
Shiota et al., "I want to Know the RNAi Protocol of that Animal!—Effective RNAi in Mammal Cells", Cell Engineering, vol. 22, No. 3, 2003, pp. 310-315, with English summary.
Sijen et al., "On the Role of RNA Amplification in dsRNA-Triggered Gene Silencing" Cell 107:465-476, 2001.
Grounds of Appeal filed by Appellant Silence Therapeutics AG, on Nov. 23, 2010, against German Patent No. DE 10066235.8, 48 pages.
Notice of Opposition to European Patent EP 1550719 filed by Silence Therapeutics AG, filed Sep. 24, 2009, 35 pages.
Petition by Silence Therapeutics in opposition proceedings for German Patent No. 10066235.8 (May 25, 2009).
Submission by Silence Therapeutics in the opposition proceedings of European Patent No. 1 214 945 (Nov. 20, 2008).
Notice of Opposition to German Application No. DE 10066235, filed by Silence Therapeutics, AG on Jul. 10, 2008, 34 pages.
Notice of Opposition to German Application No. DE 100 66 235, filed by Silence Therapeutics AG on Jul. 10, 2008.
Notice of Opposition by Silence Therapeutics against DE 100 80 167.6 (Jun. 20, 2008).
Notice of Opposition by Sirna against DE 100 80 167.6 (Jun. 20, 2008).
Simons et al., "Translational Control of IS10 Transposition" Cell 34:683-691, 1983.
Statement of Grounds and Particulars of Opposition to Australian Patent No. 778474, filed by Sirna Therapeutics, Inc. on Aug. 29, 2008.
Statement of Grounds and Particulars of Opposition to Australian Application No. 778474 filed by Sirna Therapeutics, Inc. (Jun. 1, 2009) (Clean Copy).
Written Submission by Sirna Therapeutics in Opposition proceedings for DE 100 80 167.6 (Mar. 4, 2009).
Statement of Grounds and Particulars of Opposition to Australian Patent Application No. 2005201044, filed by Sirna Therapeutics (Dec. 1, 2008).
Response to Summons to Attend Oral Proceedings pursuant to Rule 115(1) issued on Oct. 12, 2012, filed by Patentee Alnylam Europe AG on Jan. 7, 2013, for European Patent Application No. EP 02003683.6/ EP 1214945, 27 Pages.
Statutory Declaration A by Fiona H. Cameron, Opposition by Sirna Therapeutics against Australian Patent Application No. AU 2005201044, Nov. 20, 2012, 33 Pages.
Statutory Declaration A by Fiona H. Cameron, Opposition by Sirna Therapeutics against Australian Patent Application No. AU 2005201044, Nov. 20, 2012, 13 Pages.
Request that patent be revoked in its entirety, in Opposition against European Patent 1214945, filed with European Patent Office Opposition Division, filed by Opponent 1, Sirna Therapeutics on Aug. 16, 2011, 49 Pages.
Statement of Grounds & Particulars of Opposition filed by Sima Therapeutics, Inc., on Aug. 23, 2011, for Australian Patent Application No. AU 778474, 9 pages.
Response to Preliminary Opinion of the Board of Appeal for European Patent EP 1214945, filed by Sirna Therapeutics, Inc., filed on Apr. 16, 2010, 10 pages.
Notice of Opposition to Australian patent application No. AU 2008202208 filed by Sirna Therapeutics, Inc., filed on Jan. 29, 2010, 1 page.
Statement of Grounds & Particulars of Opposition to Australian patent application No. AU 2008202208 filed by Sirna Therapeutics, Inc., filed on Apr. 29, 2010, 28 pages.
Statutory Declaration by David Keith Myers dated Aug. 2, 2010, filed by Sirna Therapeutics, Inc., in opposition to Australia Patent No. AU 778474, 3 pages.
Response to Notice of Opposition to European Patent EP 1550719 filed by Alnylam Europe AG, filed Mar. 15, 2010, 40 pages.
Statutory Declaration by David Keith Myers dated Nov. 7, 2008, filed by Sirna Therapeutics, Inc., in opposition to Australia Patent No. AU 778474, 16 pages, list of journals published before the end of 1999 which cite a journal article authored by Andrew Fire and co-workers, and published in the journal Nature on Feb. 19, 1998.
Statutory Declaration by David Keith Myers dated Nov. 7, 2008, filed by Sirna Therapeutics, Inc., in opposition to Australia Patent No. AU 778474, 3 pages, list of patent publications having an earliest claimed priority date of Nov. 24, 1999 or earlier, which cite Fire, A., et al., (1998), Potent and specific genetic interference by double-stranded RNA in *Caenorhabditis eleqans*, Nature 391: 806-811.
Response to patentee's Grounds of Appeal filed by Sirna Therapeutics AG for European Patent EP 1214945, filed Dec. 23, 2009, 60 pages.
Notice of Opposition to European Patent Application No. EP 05002454.6, filed by Sirna Therapeutics, filed on Sep. 21, 2009, 42 Pages.
Submission by Sirna Therapeutics in the opposition proceedings of European Patent No. 1 214 945 (Nov. 20, 2008).
Submission by Sirna Therapeutics in opposition to European Patent No. 1 144 623 (Nov. 6, 2008).
Document by Sirna Therapeutics et al. in opposition proceedings for German Patent No. 10066235.8 (Dec. 9, 2008).
Submission by Sirna Therapeutics in opposition to European Patent No. 1 144 623 (Jun. 12, 2008).
Submission by Sirna Therapeutics in the opposition proceedings of European Patent No. 1 214 945 (Jan. 4, 2008).
Submission by Sirna Therapeutics in opposition proceedings for European Patent No. 11 44 623 (Apr. 20, 2006—Isenbruck, Bosl, Horshchler, Wichmann, Huhn).
Submission by Sirna Therapeutics in opposition proceedings for European Patent No. 11 44 623 (Apr. 20, 2006—Uexkull & Stolberg).
Notice of opposition by Sirna Therapeutics against European Patent No. 1 214 945 (Mar. 7, 2006).
Notice of Opposition by Sirna Therapeutics against European Patent No. 11 44 623 (May 28, 2003).

(56) References Cited

OTHER PUBLICATIONS

Submission by Silence Therapeutics in Opposition proceedings for DE 100 80 167.6 (Feb. 17, 2009).
Summons to attend oral proceedings in the opposition proceedings of European Patent No. 1 214 945 (May 6, 2008).
Skripkin et al., "Psoralen crosslinking between human immunodeficiency virus type 1 RNA and primer tRNA$_3^{Lsy}$," Nucleic Acids Res., 24(3):509-514 (1996).
Skorski et al., "Suppression of Philadelphia Leukemia cell growth in mice by BCR-ABL antisense oligodeoxynucleotide" Proc. Natl. Acad. Sci. USA 91 :4504-4508 (1994).
Sledz et al., "RNA Interference and Double-Stranded RNA Activated Pathways" Biochemical Society Transactions 32:956-956, 2004.
Sledz et al., "Activation of the interferon system by short-interfering RNAs," Nat. Cell Biol., 5(9):834-839 (2003).
Soeda, E., et al., "Enhancement by polylysine of transient, but not stable, expression of genes carried into cells by polyoma VP1 pseudocapsids," Gene Therapy (1998), 5: 1410-1419.
Soutschek et al., "Therapeutic silencing of an endogenous gene by systemic administration of modified siRNAs," Nature. 432:173-178 (2004).
Sporlein, B., et al., "Lipofectin: direct gene transfer to higher plants using cationic liposomes," Theoretical and Applied Genetics (1991), 83: 1-5.
Sproat, B., "Chapter 6: Synthesis of 2'-0-Alkyloligoribonucleotides," Methods in Molecular Biology 20, Edited by Sudhir Agrawal, Humana Press, NJ: 115-142 (1993).
Sproat, B. et al, "Chapter 18: 2-0-Alkyloligoribonucleotides," Antisense Research and Applications, Edited by Stanley Crooke and Bernard Lebleu, CRC Press, 351-362 (1993).
Statutory Declaration by Martin Edward O'Brien of Spruson and Ferguson in the matter of Opposition to Australian Patent No. 778474, filed by Sirna Therapeutics, Inc. on Sep. 9, 2005.
Statutory Declaration dated Aug. 17, 2010 by David M. Stalker with Exhibits OMS-A to DMS-C and Exhibits DMS-41 to DMS-74 thereto in respect of opposition to accepted Australian Patent Application No. 2005201044, 30 pages.
Declaration of David M. Stalker filed in opposition proceedings for Australian Patent 778474 (Nov. 4, 2008) (45 pages).
Declaration of David M. Stalker filed in opposition proceedings for Australian Patent 778474 (Nov. 4, 2008) (17 pages).
Stark, G., et al., "How Cells Respond to Interferons," Annu. Rev. Biochem., 1998, vol. 67, pp. 227-264.
Stetler-Stevenson et al., "Tumor Cell Interactions with the Extracellular Matrix During Invasion and Metastasis" Annu. Rev. Cell Biol. 9:541-573 (1993).
Strauss, "Candidate 'Gene Silencers' Found," Science, 286:886 (1999).
Strauss; Science, vol. 286:886• "Candidate 'Gene Silencers' Found" Oct. 29, 1999.
Stryer, L., Biochemistry, Part 1 Molecular Design of Life, Chapter 4 DNA and RNA: Molecules of Heredity, 1988, pp. 80-82.
Strasser et al., "Apoptosis Signaling" Annu. Rev. Biochem. 69:217-245 (2000).
Sui, G., et al., "A DNA vector-based RNAI technology to suppress gene expression in mammalian cells," Proc. Natl. Acad. Sci. USA, Apr. 16, 2002, pp. 5515-5520, vol. 99, No. 8.
Summerton, J., et al., "Morpholino Antisense Oligomers: Design, Preparation, and Properties," Antisense & Nucleic Acid Drua Development, 1997, pp. 187-195, vol. 7.
Suntharalingam, G., et al., "Cytokine Storm in a Phase 1 Trial of the Anti-CD28 Monoclonal Antibody TGN1412," New Enaland Journal of Medicine (2006), 355(10): 1018-1028.
Svinarchuk et al., "Inhibition of HIV proliferation in MT-4 cells by antisense oligonucleotide conjugated to lipophilic groups" Biochimie 75:49-54 (1993).
Tachibana, R., et al., "Quantitative Analysis of Correlation between Number of Nuclear Plasmids and Gene Expression Activity after Transfection with Cationic Liposomes," Pharmaceutical Research, Apr. 2002, pp. 337-381, Apr. 2002, vol. 19, No. 4.

Takayama et al., "Antisense RNA" Critical Reviews in Biochemistry and Molecular Biology 25:155-184, 1991.
Thomson et al., "Activity of hammerhead ribozymes containing non-nucleotide linkers" Nucleic Acids Res. 21:5600-5603, 1993.
Thompson, J. D., "Shortcuts from gene sequence to function," Nature Biotechnology, 17:1158-1159 (1999).
Thomson et al., "Synthesis and Properties of Diuridine Phosphate Analogues Containing Thio and Amino Modifications" J. Org. Chem. 61:6273-6281 (1996).
Tijsterman, M. et al., 2002, "The Genetics of RNA Silencing", Annu. Rev. Genet., 36:489-519.
Timmons et al., "Specific interference by ingested dsRNA," Nature, 395:854 ( 1998).
Timmons et al.; Nature, 395(6705:854); Specific Interference by Ingested dsRNN' Oct. 29, 1998.
Tolun et al., "Direct Repeats of the F Plasmid incC Region Express F Incompatibility" Cell 24: 687-694 (1981).
Touze, A., et al., "In vitro gene transfer using human papillomavirus-like particles," Nucleic Acids Res. (1998) 26(5): 1317-1323.
Tsutsui et al., "Role of Nine Repeating Sequences of the Mini-F Genome for Expression of F-Specific Incompatibility Phenotype and Copy Number Control" Journal of Bacteriology 155:337-344, 1983.
Tuschl et al., "Targeted mRNA degradation by double-stranded RNA in vitro," Genes Dev., 13:3191-3197 (1999).
Tuschl et al. (Dec. 1999) Genes and Dev. 13 :3191-7.
Uhlmann E et al: "Antisense Oligonucleotides: A New Therapeutic Principle" Chemical Reviews, US, American Chemical Society. E Ston, Bd. 90, Nr. 4, Jun. 1, 1990, pp. 543-584, XP000141412 ISSN: 0009-2665.
Uhlmann, E. et al. "Antisense Nucleotides: A New Therapeutic Principal" Chemical Reviews, American Chemical Society, Easton, US vol. 90, No. 4, Jun. 1, 1990, pp. 543-584, ISSN:0009-2665.
Uhlenbeck, "A Small Catalytic Oligoribonucleotide" Nature 325:596-600, 1987.
U.S. Appl. No. 60/117,635, filed Jan. 28, 1999.
U.S. Appl. No. 60/175,440, filed Jan. 11, 2000.
Van Der Krol, A., et al., "An anti-sense chalcone synthase gene in transgenic plants inhibits fewer pigmentation," Nature, Jun. 30, 1988, pp. 866-869, vol. 333.
Van Beusechem et al., "Long-term expression of human adenosine deaminase in rhesus monkeys transplanted with retrorirus-infected bone-marrow cells" Proc. Natl. Acad. Sci. USA 89:7640-7644 (1992).
Van Etten, "Pathoogenesis and treatment of Ph+ leukemia: recent insights from mouse models" Curr. Opin_Hematol. 8:224-230 (2001 ).
Verma, et al., "Gene therapy—promises, problems, and prospects," Nature, 389:239-242 (1997).
Vickers et al., "Efficient Reduction of Target RNAs by Small Interfering RNA and RNase H-dependent Antisense Agents. A Comparative Analysis" J. Biol. Chem. 278: 7108-7118 (2003).
Voinnet et al., "Systemic signalling; in gene silencing.," Nature, 389:553 (1997).
Voinnet, 0. and Baulcombe, D. C., Nature (1997), 398:553.
Wacheck et al., "Small Interfering RNA Targeting Bcl-2 Sensitizers Malignant Melanoma" Oligonucleotides, vol. 13 (5):393-400 (2003).
Wagner, et al., Feb. 19, 1998, Double-stranded RNA poses puzzle, Nature, 391: 744-745.
Wagner, et al., "Double-stranded RNA poses puzzle," Nature, 391:744-745 (1998).
Wagner, "The state of the art in antisense research" Nat Med. 1:1116-1118 (1995).
Wang, L., et al., "Preclinical Characterization of an Anti-tat Ribozyme for Therapeutic Application," Human Gene Therapy, Jun. 10, 1998, pp. 128-1291, vol. 9.
Wang, S., et al., "Delivery of antisense oligodeoxyribonucleotides against the human epidermal growth factor receptor into cultured KB cells with liposomes conjugated to folate via polyethylene glycol," Proc. Nat. Acad. Sci., Biochemistrv, Apr. 1995, pp. 3318-3322.
Wang, S., et al. "Circular RNA oligonucleotides. Synthesis, nucleic acid binding properties, and a comparison with circular DNAs," Nucleic Acids Research, 22:2326-2333 (1994).

(56) References Cited

OTHER PUBLICATIONS

Wang, Z. et al., "RNA conformation in the Tat-TAR complex determined by site-specific photo-cross-linking," Biochem, 35:6491-6499 (1996).
Wargelius et al., "Double-Stranded RNA Induces Specific Developmental Defects in Zebrafish Embryos," Biochem. Biophys. Res. Commun., 263:156-161 (1999).
Wargelius, et al., 1999, Double-stranded RNA induces specific developmental defects in zebrafish embryos, Biochem BioDhys Res Com., 263: 156-161.
Waterhouse et al., "Virus resistance and gene silencing in plants can be induced by simultaneous expression of sense and antisense RNA," Proc. Natl. Acad. Sci. USA. 95:13959-13964 (1998).
Waterhouse et al.; PNAS, vol. 95:13959-13964, "Virus resistance and gene silencing in plants can be / induced by simultaneous expression of sense and antisense RNA" Nov. 1998.
Watkins, K. P., et al., "In vivo UV cross-linking of U snRNAs that participate in trypanosome trans-splicing," Genes & Development, 5:1859-1869 (1991).
Wengel, J., "Synthesis of 3'-C- and 4'-C-branched oligodeoxynucleotides and the development of locked nucleic acid (LNA)," Acc. Chem. Res., 32:301-310 (1999).
Wess et al., "Early days for RNAi," BioCentury, 11(12):AI-A8 (2003).
Wianny et al., "Specific interference with gene function by double-stranded RNA in early mouse development." Nat. Cell Biol., 2:70-75 (2000).
Wikipedia, "File: NIH 3T3.jpg," NIH/3T3 Mouth Embry Fibroblast, May 9, 2007, 1 page, can be retrieved at //commons.wikimedia.ora/wiki/File: NIH 3T3.inn.
Wild et al., "The 2A structure of helix 6 of the human signal recognition particle RNA" Structure 7:1345-1352, 1999.
Williams et al., "Thermodynamic Comparison of the Salt Dependence of Natural RNA Hairpins and RNA Hairpins with Non-Nucleotide Spacers" Biochemistry 35:14665-14670 (1996).
Wilson et al., "Retrovirus-mediated transduction of adult hepatocytes" Proc. Natl. Acad. Sci. USA 85:3014-3018 (1988).
Wink, Molekulare Biotechnologie, Wiley-VCH, 2004, 557-577.
Wong et al., "Modeling Philadelphia chromosome positive leukemias" Oncogene 20:5644-5659 (2001).
Xie, Y., et al., "Efficacy of Adenovirus-mediated CD/5-FC and HSV-1 Thymidine Kinase/Ganciclovir Suicide Gene Therapies Concomitant with p53 Gene Therapy1 ,"Clinical Cancer Research, Dec. 1999, pp. 4224-4232, vol. 5.
Yang et. Al., "Evidence that processed small dRNAs may mediate sequence-specific mRNA degradation during RNAi in *Drosophila* embryos" Current Biology 10:1191-1200, 2000.
Yang Shi, et al.; Genes & Development, vol. 12, (No. 7):943-955; "A CBP/p300 homolog specifies multiple differentiation oathwavs in *Caenorhabditis elegans*" Apr. 1, 1998.
Yokota, "Tumor progression and metastasis" Carcinogenesis 21:497-503 (2000).
Yu, J. et al:, (2002), "RNA interference by expression of short-interfering RNAs and hairpin RNAs in mammalian cells", PNAS, 99(9):6047-6052.
Zamecnik, P.C., et al., "Inhibition of *Rous sarcoma virus* replication and cell transformation by a specific oliqodeoxynucleotide," Proc. Natl. Acad. Sci. USA (1978), 75(1 ): 280-284.
Zamore et al. "Evidence that siRNAs function as guides not primers in the *Drosophila* and human RNAi pathways." Mol. Cell, 10:537-48 (2002).
Zamore et al., "RNAi: Double-Stranded RNA Directs the ATP-Dependent Cleavage of mRNA at 21 to 23 Nucleotide Intervals," Cell, 101:25-33 (2000).
Zelphati, O., et al., "Antisense oligonucleotides in solution of encapsulated in immunoliposomes inhibit replication of HIV-1 by several different mechanisms," Nucleic Acids Research, 1994, pp. 4307-4314, vol. 22, No. 20.
Zeng et al., "RNA interference in human cells is restricted to the cytoplasm," RNA, 8;855-860 (2002).

Zeng et al., "The Fetal Origin of B-Precursor Leukemia in the Eu-ret Mouse" Blood 92:3529-3536 (1988).
Zhao et al., "Double-Stranded RNA Injection Produces Nonspecific Defects in Zebrafish," Dev. Biol., 229:215-223 (2001).
Zhang et al., "Targeted Gene Silencing by Small Interfering RNA-Based Knock-Down Technology" Current Pharmaceutical Biothechnology 5:1-7, 2004.
Zhang et al., "Single processing center models for human dicer and bacterial RNase III" Cell 118:57-68 (2004).
Zheng, L., et al., "An approach to genomewide screens of expressed small interfering RNAs in mammalian cells," Proc. Natl. Acad. Sci. USA, Jan. 6, 2004, pp. 135-140, vol. 101, No. 1.
Zheng et al., "Activation of the protein kinase PKR by short double-stranded R.NAs with single-stranded tails." RNA, 10:1934-1945 (2004).
Zwieb, C. et al., "Evidence for RNA-RNA cross-linked formation in *Escherichia coli* ribosomes," Nucleic Acids Research, 5:2705-2720 (1978).
International Search Report PCT/DE 00/00244.
Office Action for U.S. Appl. No. 10/382,395 Oct. 5, 2009, 9 Pages.
Office Action for U.S. Appl. No. 10/382,768, Nov. 26, 2010, 7 pages.
Office Action for U.S. Appl. No. 10/382,768, Feb. 5, 2010, 12 Pages.
Office Action for U.S. Appl. No. 10/383,099, Mar. 30, 2011, 10 pages.
Office Action for U.S. Appl. No. 10/383,099, Dec. 17, 2009, 9 Pages.
Office Action for U.S. Appl. No. 10/383,099, Oct. 15, 2010, 19 pages.
Office Action dated Aug. 26, 2011, for U.S. Appl. No. 10/383,099, 5 pages.
Office Action for U.S. Appl. No. 10/612,179 Dec. 17, 2009, 9 Pages.
Office Action dated Jun. 17, 2011, for U.S. Appl. No. 10/612,179, 11 Pages.
Office Action for U.S. Appl. No. 10/612,179, Oct. 20, 2010, 24 pages.
Office Action for U.S. Appl. No. 11/982,305, Sep. 3, 2010, 10 pages.
Office Action for U.S. Appl. No. 11/982,305, Feb. 11, 2011, 13 pages.
Office Action for U.S. Appl. No. 11/982,325, Oct. 6, 2010, 11 pages.
Office Action for U.S. Appl. No. 11/982,325, Mar. 18, 2011, 12 pages.
Office Action for U.S. Appl. No. 11/982,328, Oct. 6, 2010, 11 pages.
Office Action for U.S. Appl. No. 11/982,345, Mar. 18, 2011, 14 pages.
Office Action for U.S. Appl. No. 11/982,425, Sep. 2, 2010, 10 pages.
Office Action for U.S. Appl. No. 11/982,425, Feb. 11, 2011, 13 pages.
Office Action for U.S. Appl. No. 11/982,434, Oct. 6, 2010, 11 pages.
Office Action for U.S. Appl. No. 11/982,434, Mar. 18, 2011, 12 pages.
Office Action for U.S. Appl. No. 11/982,411, Oct. 6, 2010, 12 pages.
Office Action for U.S. Appl. No. 11/982,441, Mar. 18, 2011, 12 pages.
Office Action for U.S. Appl. No. 13/656,540, mailed Nov. 22, 2013, 13 Pages.
Office Action for U.S. Appl. No. 13/656,548, mailed Dec. 17, 2013, 14 Pages.
Office Action for U.S. Appl. No. 13/753,438, Apr. 26, 2013, 14 Pages.
Office Action for U.S. Appl. No. 13/753,438, mailed Jan. 29, 2013, 15 Pages.
Office Action for U.S. Appl. No. 11/982,325, mailed Jul. 10, 2013, 11 Pages.
Office Action for U.S. Appl. No. 11/982,345 mailed Jul. 29, 2013, 6 Pages.
International Search Report of International Application No. PCT/EP2002/00151, Jan. 27, 2003, 7 pages.
Office Action Communication by the German Patent and Trademark Office dated Apr. 11, 2011 for German Divisional Patent Application No. 10066344.3-41, 7 pages.
Minutes of the Oral Proceedings held on Jan. 14, 2010 in Opposition to German Patent DE 10066235.8, issued by the German Patent and Trademark Office, 55 Pages.
Minutes of oral proceedings regarding opposition against German Patent DE 10066235.8, Feb. 5, 2010, 14 Pages.
Examination Report for German Divisional Patent Application No. DE 10066382.6, Apr. 8, 2011, 13 pages.
Petition regarding German Patent No. DE 10080167 filed by Silence Therapeutics AG, Mar. 17, 2009, 20 pages.

(56) References Cited

OTHER PUBLICATIONS

Record for the Oral proceedings before the Opposition Division from European Patent Office, in opposition of European Patent No. 1214945, Mar. 21, 2009, 92 Pages.
Minutes of oral proceedings for European Patent EP 1214945, May 19, 2010, 13 pages.
Summons to Attend Oral Hearing regarding opposition against European Patent EP 1214945, Feb. 26, 2010, 15 pages.
Response to Summons for oral proceedings in Opposition against EP 1214945 filed by Silence Therapeutics AG, filed on Apr. 19, 2010, 5 pages.
Decision of the Board of Appeal of May 19, 2010 in Opposition to European Patent No. EP 1214945, Jul. 20, 2010, 28 pages.
Response to European Search Opinion filed with the European Patent Office on Feb. 23, 2012 for European Divisional Patent Application No. EP 10011217.6, 6 Pages.
Summons to attend oral proceedings pursuant to Rule 115(1) EPC issued by the European Patent Office on Nov. 25, 2011, for Opposition against European Patent No. EP 1550719, 50 Pages.
Office Action Communication pursuant to Article 94(3) EPC dated Jul. 8, 2011, for European Patent Application No. EP 06025389.5, 8 pages.
Reply to Office Action per article 94 (3) EPC of Jul. 8, 2011, filed on Nov. 17, 2011, European Patent Application No. EP 06025389.5, 5 pages.
Communication issued by European Patent Office on Apr. 23, 2012 with Petition by Opponent I, Opposition against EP 1214945, 2 pages.
Document in opposition proceedings for EP Patent No. 1214945 (Mar. 31, 2009).
Communication in opposition proceedings for German Patent No. 10066235.8 (Jun. 23, 2009).
Notice in accordance with article 94 (3) EPC for European Patent Application No. EP 06025389.5, Oct. 8, 2013, 10 Pages.
Notice in accordance with article 94 (3) EPC for European Patent Application No. EP 10011217.6, Oct. 9, 2013, 11 pages.
Extended European Search Report and Written Opinion, mailed Aug. 8, 2011 for European Patent Application No. EP 10011217.6, 21 Pages.
Decision of Rejection for Japan Patent Application No. 2009-002826, Mar. 9, 2010, 4 Pages.
Notice of Reasons for Rejection for Japan Patent Application No. 2009-002826, Jun. 16, 2009, 15 Pages.
Notice of Reasons for Rejection, mailed on Nov. 1, 2011, Japanese Patent Application No. JP 2009 002825, 9 Pages.
Notice of Reasons for Rejection for Japan Patent Application No. 2009-002824, Jun. 16, 2009, 15 Pages.
Decision of Rejection for Japan Patent Application No. 2009-002824, Mar. 9, 2010, 4 Pages.
Official Inquiry dated May 17, 2011, for Japanese Patent Application No. 2007-186339 (Appeal No. 2009- 11870), 10 pages.
Written Reply filed on Oct. 17, 2011, Japanese Patent Application No. JP 2007-186339, 77 pages.
Notice of Reasons for Rejection for Japanese Patent Application No. JP 2007-186339 (Appeal No. 2009-11870), May 15, 2012, 26 Pages.
Official Inquiry dated May 17, 2011, for Japanese Patent Application No. 2007-186340 (Appeal No. 2009-11715), 11 pages.
Written Reply filed on Oct. 17, 2011, Japanese Patent Application No. JP 2007-186340, 76 pages.
Notice of Reasons for Rejection for Japanese Patent Application No. JP 2007-186340 (Appeal No. 2009-11715), May 15, 2012, 24 Pages.
Official Inquiry dated May 17, 2011, for Japanese Patent Application No. 2007-186341 (Appeal No. 2009-11871), 6 pages.
Written Reply filed on Oct. 17, 2011, Japanese Patent Application No. JP 2007-186341, 70 pages.
Notice of Reasons for Rejection for Japanese Patent Application No. JP 2007-186341 (Appeal No. 2009-11871), May 15, 2012, 26 Pages.
Notice of Reasons for Rejection for Japanese Patent Application No. JP 2009-285705, Jul. 17, 2012, 13 Pages.
Office Action for Japanese Patent Application No. JP 2009-285705, Apr. 2, 2013, 6 Pages.
Notice of Reasons for Rejection for Japanese Patent Application No. JP 2009-285706, Jul. 17, 2012, 10 Pages.
Summons to oral proceedings pursuant to Rule 115 (1) EPC, European Patent Appl. No. EP 02003683, Jul. 23, 2012, 28 Pages.
Notice of Acceptance for Australian patent application No. AU 2008202208, Oct. 19, 2009, 3 pages.
Submission by Silence Therapeutics against DE 100 80 167.6 on Feb. 20, 2009.27,2009.
Response to three Notices of Opposition submitted by Alnvlam Europe AG in German Patent No. 100 66235.8-41 (Feb. 4, 2009), including list of documents cited (translation enclosed).
Statement of Grounds and Particulars of Opposition to Australian Patent No. 778474, filed by Sirna Therapeutics, Inc. on Sep. 9, 2005.
Statutory Declaration by Martin Edward O'Brien ofSpruson and Ferguson in the matter of Opposition to Australian Patent No. 778474, filed by Sirna Therapeutics, Inc. on Sep. 9, 2005.
Kreutzer, R., Limmer, S., Application No. 199 03 713.2, "Medication for Inhibiting Expression of a Defined Gene,"English translation of priority document for PCT/DE 00/00244, German Patent and Trademark Office, May 11, 2000.
United States Office Action for U.S. Appl. No. 10/612,179, Oct. 27, 2011, 5 pages.
United States Office Action for U.S. Appl. No. 10/612,179, Jan. 27, 2012, 5 pages.
United States Office Action for U.S. Appl. No. 10/612,179, Jul. 13, 2005, 9 pages.
United States Office Action for U.S. Appl. No. 10/612,179, Oct. 16, 2007, 14 pages.
United States Office Action for U.S. Appl. No. 10/612,179, Aug. 7, 2006, 8 pages.
United States Office Action for U.S. Appl. No. 10/612,179, Jan. 25, 2006, 10 pages.
United States Office Action for U.S. Appl. No. 10/612,179, May 1, 2009, 13 pages.
United States Office Action for U.S. Appl. No. 10/612,179, Sep. 23, 2008, 12 pages.
United States Office Action for U.S. Appl. No. 10/612,179, Mar. 10, 2005, 12 pages.
United States Office Action for U.S. Appl. No. 10/612,179, May 1, 2008, 3 pages.
United States Office Action for U.S. Appl. No. 09/889,802, Mar. 10, 2004, 6 pages.
United States Office Action for U.S. Appl. No. 09/889,802, Feb. 3, 2004, 6 pages.
United States Office Action for U.S. Appl. No. 09/889,802, Dec. 15, 2003, 11 pages.
United States Office Action for U.S. Appl. No. 09/889,802, Jun. 14, 2004, 9 pages.
United States Office Action for U.S. Appl. No. 09/889,802, Jun. 1, 2005, 10 pages.
United States Office Action for U.S. Appl. No. 09/889,802, Jun. 25, 2003, 12 pages.
United States Office Action for U.S. Appl. No. 09/889,802, Apr. 7, 2003, 13 pages.
United States Office Action for U.S. Appl. No. 09/889,802, Aug. 21, 2003, 3 pages.
United States Office Action for U.S. Appl. No. 13/656,513, Jun. 19, 2014, 26 pages.
United States Office Action for U.S. Appl. No. 13/656,540, Jan. 14, 2015, 29 pages.
United States Office Action for U.S. Appl. No. 13/656,540, May 12, 2014, 14 pages.
United States Office Action for U.S. Appl. No. 13/656,548, Jan. 2, 2015, 17 pages.
United States Office Action for U.S. Appl. No. 13/656,548, May 29, 2014, 12 pages.
Proud C. G., "PKR: a new name and new roles", TIBS 20, Jun. 1995, pp. 241-246, Elsevier Science Ltd.

SEQUENCE LISTING

```
<160> NUMBER OF SEQ ID NOS: 8

<210> SEQ ID NO 1
<211> LENGTH: 45
<212> TYPE: DNA
<213> ORGANISM: Artificial Sequence
<220> FEATURE:
<223> OTHER INFORMATION: Description of the artificial sequence:
      EcoRI cleavage site, T7 RNA Polymerase promoter

<400> SEQUENCE: 1
ggaattctaa tacgactcac tatagggcga tcagatctct agaag            45

<210> SEQ ID NO 2
<211> LENGTH: 50
<212> TYPE: DNA
<213> ORGANISM: Artificial Sequence
<220> FEATURE:
<223> OTHER INFORMATION: Description of the artificial sequence:
      BamHI cleavage site, SP6 RNA Polymerase promoter
```

```
<400> SEQUENCE: 2
gggatccatt taggtgacac tatagaatac ccatgatcgc gtagtcgata            50

<210> SEQ ID NO 3
<211> LENGTH: 340
<212> TYPE: RNA
<213> ORGANISM: Artificial Sequence
<220> FEATURE:
<223> OTHER INFORMATION: Description of the artificial sequence:
      RNA which corresponds to a sequence from the positive control DNA
      of the HeLa Nuclear Extract in vitro transcription kit from
      Promega

<400> SEQUENCE: 3
ucagaucucu agaagcuuua augcgguagu uuaucacagu uaaauugcua acgcagucag    60
gcaccgugua ugaaaucuaa caaugcgcuc aucgucaucc ucggcaccgu cacccuggau   120
gcuguaggca uaggcuuggu uaugccggua cugccgggcc ucuugcggga uaucguccau   180
uccgacagca ucgccaguca cuauggcgug cugcuagcgc uauaugcguu gaugcaauuu   240
cuaugcgcac ccguucucgg agcacugucc gaccgcuuug gccgccgccc aguccugcuc   300
gcuucgcuac uuggagccac uaucgacuac gcgaucaugg                        340

<210> SEQ ID NO 4
<211> LENGTH: 363
<212> TYPE: DNA
<213> ORGANISM: Artificial Sequence
<220> FEATURE:
<223> OTHER INFORMATION: Description of the artificial sequence:
      DNA which corresponds to a sequence from the positive control DNA
      of the HeLa Nuclear Extract in vitro transcription kit from
      Promega

<400> SEQUENCE: 4
tcagatctct agaagcttta atgcggtagt ttatcacagt taaattgcta acgcagtcag    60
gcaccgtgta tgaaatctaa caatgcgctc atcgtcatcc tcggcaccgt cacccpggat   120 gctgtaggca taggcttggt tatgccggta ctgccgggcc tcttgcggga tatcgtccat   180
tccgacagca tcgccagtca ctatggcgtg ctgctagcgc tatatgcgtt gatgcaattt   240
ctatgcgcac ccgttctcgg agcactgtcc gaccgctttg gccgccgccc agtcctgctc   300
gcttcgctac ttggagccac tatcgactac gcgatcatgg cgaccacacc cgtcctgtgg   360
atc                                                                363

<210> SEQ ID NO 5
<211> LENGTH: 315
<212> TYPE: RNA
<213> ORGANISM: Artificial Sequence
<220> FEATURE:
<223> OTHER INFORMATION: Description of the artificial sequence:
      Sequence from the YFP gene

<400> SEQUENCE: 5
auggugagca agggcgagga gcuguucacc ggggugguge ccauccuggu cgagcuggac    60
ggcgacguaa acggccacaa guucagcgug uccggcgagg gcgagggcga ugccaccuac   120
ggcaagcuga cccugaaguu caucugcacc accggcaagc ugcccgugcc cuggcccacc   180
cucgugacca cccugaccua cggcgugcag ugcuucagcc gcuaccccga ccacaugaag   240
cagcacgacu ucuucaaguc cgccaugccc gaaggcuacg uccaggagcg caccaucuuc   300
uucaaggacg acggc                                                   315
```

```
<210> SEQ ID NO 6
<211> LENGTH: 52
<212> TYPE: DNA
<213> ORGANISM: Artificial Sequence
<220> FEATURE:
<223> OTHER INFORMATION: Description of the artificial sequence:
      EcoRI cleavage site, T7 RNA Polymerase promoter, complementary
      region to the YFP gene

<400> SEQUENCE: 6
ggaattctaa tacgactcac tatagggcga atggtgagca agggcgagga gc            52

<210> SEQ ID NO 7
<211> LENGTH: 53
<212> TYPE: DNA
<213> ORGANISM: Artificial Sequence
<220> FEATURE:
<223> OTHER INFORMATION: Description of the artificial sequence:
      BamHI cleavage site, SP6 RNA Polymerase promoter, complementary
      region to the YFP gene

<400> SEQUENCE: 7
gggatccatt taggtgacac tatagaatac gccgtcgtcc ttgaagaaga tgg           53

<210> SEQ ID NO 8
<211> LENGTH: 21
<212> TYPE: RNA
<213> ORGANISM: Artificial Sequence
<220> FEATURE:
<223> OTHER INFORMATION: Description of the artificial sequence:
      RNA which corresponds to a sequence from the YFP gene

<400> SEQUENCE: 8
ucgagcugga cggcgacgua a                                              21
```

METHOD AND MEDICAMENT FOR INHIBITING THE EXPRESSION OF A GIVEN GENE

CROSS-REFERENCE TO RELATED APPLICATIONS

This application is a continuation of U.S. patent application Ser. No. 13/656,513, filed Oct. 19, 2012, which is a continuation of U.S. patent application Ser. No. 11/982,325, filed Oct. 31, 2007, which is a continuation of U.S. patent application Ser. No. 10/612,179, filed Jul. 2, 2003, now issued, which is a divisional of U.S. patent application Ser. No. 09/889,802, filed Sep. 17, 2001, now abandoned, which is the National Stage of International Patent Application No. PCT/DE00/00244, filed Jan. 29, 2000, which claims priority to German Patent Application No. DE19903713.2, filed Jan. 30, 1999, and German Patent Application No. DE19956568.6, filed Nov. 24, 1999. The contents of these prior applications are hereby incorporated by reference in their entirety for all purposes.

The invention relates to a medicament and to a use of double-stranded oligoribonucleotides and to a vector encoding them.

Such a method is known from WO 99/32619, which was unpublished at the priority date of the present invention. The known process aims at inhibiting the expression of genes in cells of invertebrates. To this end, the double-stranded oligoribonucleotide must exhibit a sequence which is identical with the target gene and which has a length of at least 50 bases. To achieve efficient inhibition, the identical sequence must be 300 to 1000 base pairs in length. Such an oligoribonucleotide is complicated to prepare.

DE 196 31 919 C2 describes an antisense RNA with specific secondary structures, the antisense RNA being present in the form of a vector encoding it. The antisense RNA takes the form of an RNA molecule which is complementary to regions of the mRNA. Inhibition of the gene expression is caused by binding to these regions. This inhibition can be employed in particular for the diagnosis and/or therapy of diseases, for example tumor diseases or viral infections.—The disadvantage is that the antisense RNA must be introduced into the cell in an amount which is at least as high as the amount of the mRNA. The known antisense methods are not particularly effective.

U.S. Pat. No. 5,712,257 discloses a medicament comprising mismatched double-stranded RNA (dsRNA) and bioactive mismatched fragments of dsRNA in the form of a ternary complex together with a surfactant. The dsRNA used for this purpose consists of synthetic nucleic acid single strands without defined base sequence. The single strands undergo irregular base pairing, also known as "non-Watson-Crick" base pairing, giving rise to mismatched double strands. The known dsRNA is used to inhibit the amplification of retroviruses such as HIV. Amplification of the virus can be inhibited when non-sequence-specific dsRNA is introduced into the cells. This leads to the induction of interferon, which is intended to inhibit viral amplification. The inhibitory effect, or the activity, of this method is poor.

It is known from Fire, A. et al., NATURE, Vol. 391, pp. 806 that dsRNA whose one strand is complementary in segments to a nematode gene to be inhibited inhibits the expression of this gene highly efficiently. It is believed that the particular activity of the dsRNA used in nematode cells is not due to the antisense principle but possibly on catalytic properties of the dsRNA, or enzymes induced by it.—Nothing is mentioned in this paper on the activity of specific dsRNA with regard to inhibiting the gene expression, in particular in mammalian and human cells.

The object of the present invention is to do away with the disadvantages of the prior art. In particular, it is intended to provide as effective as possible a method, medicament or use for the preparation of a medicament, which method, medicament or use is capable of causing particularly effective inhibition of the expression of a given target gene.

This object is achieved by the features of the claims presented here. Advantageous embodiments can be seen from the claims presented here.

In accordance with the method-oriented inventions, it is provided in each case that the region I which is complementary to the target gene exhibits not more than 49 successive nucleotide pairs.

Provided in accordance with the invention are an oligoribonucleotide or a vector encoding therefor. At least segments of the oligoribonucleotide exhibit a defined nucleotide sequence. The defined segment may be limited to the complementary region I. However, it is also possible that all of the double-stranded oligoribonucleotide exhibits a defined nucleotide sequence.

Surprisingly, it has emerged that an effective inhibition of the expression of the target gene can be achieved even when the complementary region I is not more than 49 base pairs in length. The procedure of providing such oligoribonucleotides is less complicated.

In particular, dsRNA with a length of over 50 nucleotide pairs induces certain cellular mechanisms, for example the dsRNA-dependent protein kinase or the 2-5 A system, in mammalian and human cells. This leads to the disappearance of the interference effect mediated by the dsRNA which exhibits a defined sequence. As a consequence, protein biosynthesis in the cell is blocked. The present invention overcomes this disadvantage in particular.

Furthermore, the uptake of dsRNA with short chain lengths into the cell or into the nucleus is facilitated markedly over longer-chain dsRNAs.

It has proved advantageous for the dsRNA or the vector to be present packaged into micellar structures, preferably in liposomes. The dsRNA or the vector can likewise be enclosed in viral natural capsids or in chemically or enzymatically produced artificial capsids or structures derived therefrom. The abovementioned features make it possible to introduce the dsRNA or the vector into given target cells.

In a further aspect, the dsRNA has 10 to 1000, preferably 15 to 49, base pairs. Thus, the dsRNA can be longer than the region I, which is complementary to the target gene. The complementary region I can be located at the terminus or inserted into the dsRNA. Such dsRNA or a vector provided for coding the same can be produced synthetically or enzymatically by customary methods.

The gene to be inhibited is expediently expressed in eukaryotic cells. The target gene can be selected from the following group: oncogene, cytokin gene, Id protein gene, developmental gene, prion gene. It can also be expressed in pathogenic organisms, preferably in plasmodia. It can be part of a virus or viroid which is preferably pathogenic to humans.—The method proposed makes it possible to produce compositions for the therapy of genetically determined diseases, for example cancer, viral diseases or Alzheimer's disease.

The virus or viroid can also be a virus or viroid which is pathogenic to animals or plant-pathogenic. In this case, the method according to the invention also permits the provision of compositions for treating animal or plant diseases.

In a further aspect, segments of the dsRNA are designed as double-stranded. A region II which is complementary within the double-stranded structure is formed by two separate RNA single strands or by autocomplementary regions of a topologically closed RNA single strand which is preferably in circular form.

The ends of the dsRNA can be modified to counteract degradation in the cell or dissociation into the single strands. Dissociation takes place in particular when low concentrations or short chain lengths are used. To inhibit dissociation in a particularly effective fashion, the cohesion of the complementary region II, which is caused by the nucleotide pairs, can be increased by at least one, preferably two, further chemical linkage(s).—A dsRNA according to the invention whose dissociation is reduced exhibits greater stability to enzymatic and chemical degradation in the cell or in the organism.

The complementary region II can be formed by autocomplementary regions of an RNA hairpin loop, in particular when using a vector according to the invention. To afford protection from degradation, it is expedient for the nucleotides to be chemically modified in the loop region between the double-stranded structure.

The chemical linkage is expediently formed by a covalent or ionic bond, a hydrogen bond, hydrophobic interactions, preferably van-der-Waals or stacking interactions, or by metal-ion coordination. In an especially advantageous aspect, it can be formed at at least one, preferably both, end(s) of the complementary region II.

It has furthermore proved to be advantageous for the chemical linkage to be formed by one or more linkage groups, the linkage groups preferably being poly (oxyphosphinicooxy-1,3-propanediol) and/or poly-ethylene glycol chains. The chemical linkage can also be formed by purine analogs used in place of purines in the complementary regions II. It is also advantageous for the chemical linkage to be formed by azabenzene units introduced into the complementary regions II. Moreover, it can be formed by branched nucleotide analogs used in place of nucleotides in the complementary regions II.

It has proved expedient to use at least one of the following groups for generating the chemical linkage: methylene blue; bifunctional groups, preferably bis(2-chloroethyl) amine; N-acetyl-N'-(p-glyoxyl-benzoyl)cystamine; 4-thiouracil; psoralene. The chemical linkage, can furthermore be formed by thiophosphoryl groups provided at the ends of the double-stranded region. The chemical linkage at the ends of the double-stranded region is preferably formed by triple-helix bonds.

The chemical linkage can expediently be induced by ultraviolet light.

The nucleotides of the dsRNA can be modified. This counteracts the activation, in the cell, of a double-stranded-RNA-dependent protein kinase, PKR. Advantageously, at least one 2'-hydroxyl group of the nucleotides of the dsRNA in the complementary region II is replaced by a chemical group, preferably a 2'-amino or a 2'-methyl group. At least one nucleotide in at least one strand of the complementary region II can also be a locked nucleotide with a sugar ring which is chemically modified, preferably by a 2'-O, 4'-C methylene bridge. Advantageously, several nucleotides are locked nucleotides.

A further especially advantageous embodiment provides that the dsRNA or the vector is bound to, associated with or surrounded by, at least one viral coat protein which originates from a virus, is derived therefrom or has been prepared synthetically. The coat protein can be derived from polyomavirus. The coat protein can contain the polyomavirus virus protein 1 (VP1) and/or virus protein 2 (VP2). The use of such coat proteins is known from, for example, DE 196 18 797 A1, whose disclosure is herewith incorporated.—The abovementioned features considerably facilitate the introduction of the dsRNA or of the vector into the cell.

When a capsid or capsid-type structure is formed from the coat protein, one side preferably faces the interior of the capsid or capsid-type structure. The construct formed is particularly stable.

The dsRNA can be complementary to the primary or processed RNA transcript of the target gene.—The cell can be a vertebrate cell or a human cell.

At least two dsRNAs which differ from each other or at least one vector encoding them can be introduced into the cell, where at least segments of one strand of each dsRNA are complementary to in each case one of at least two different target genes. This makes it possible simultaneously to inhibit the expression of at least two different target genes. In order to suppress, in the cell, the expression of a double-stranded-RNA-dependent protein kinase, PKR, one of the target genes is advantageously the PKR gene. This allows effective suppression of the PKR activity in the cell.

The invention furthermore provides a medicament with at least one oligoribonucleotide with double-stranded structure (dsRNA) for inhibiting the expression of a given target gene, where one strand of the dsRNA has a region I where at least segments are complementary to the target gene.—Surprisingly, it has emerged that such a dsRNA is suitable as medicament for inhibiting the expression of a given gene in mammalian cells. In comparison with the use of single-stranded oligoribonucleotides, the inhibition is already caused at concentrations which are lower by at least one order of magnitude. The medicament according to the invention is highly effective. Lesser side effects can be expected.

The invention furthermore provides a medicament with at least one vector for coding at least one oligoribonucleotide with double-stranded structure (dsRNA) for inhibiting the expression of a given target gene, where one strand of the dsRNA has a region I where at least segments are complementary to the target gene.—The medicament proposed exhibits the abovementioned advantages. By, using a vector, in particular production costs can be reduced.

In a particularly advantageous embodiment, the complementary region I has not more than 49 successive nucleotide pairs.—Surprisingly, it has emerged that an effective inhibition of the expression of the target gene can be achieved even when the complementary region I is not more than 49 base pairs in length. The procedure of providing such oligoribonucleotides is less complicated.

The invention furthermore provides a use of an oligoribonucleotide with double-stranded structure (dsRNA) for preparing a medicament for inhibiting the expression of a given target gene, where one strand of the dsRNA has a region I where at least segments are complementary to the target gene.—Surprisingly, such a dsRNA is suitable for preparing a medicament for inhibiting the expression of a given gene. Compared with the use of single-stranded oligoribonucleotides, the inhibition is already caused at concentrations which are lower by one order of magnitude when using dsRNA. The use according to the invention thus makes possible the preparation of particularly effective medicaments.

The invention furthermore provides the use of a vector for coding at least one oligoribonucleotide with double-stranded structure (dsRNA) for preparing a medicament for inhibiting the expression of a given target gene, where one strand of the dsRNA has a region I where at least segments are complementary to this target gene.—The use of a vector makes possible a particularly effective gene therapy.

With regard to advantageous embodiments of the medicament and of the use, reference is made to the description of the above features.

Figure 2:
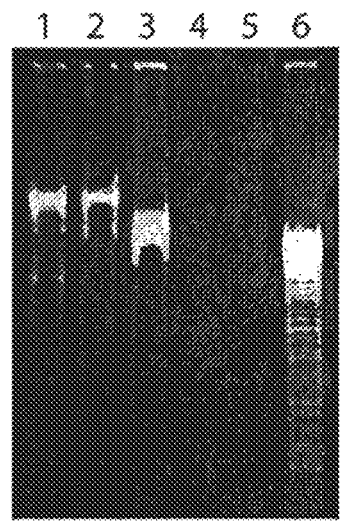
Figure 3:
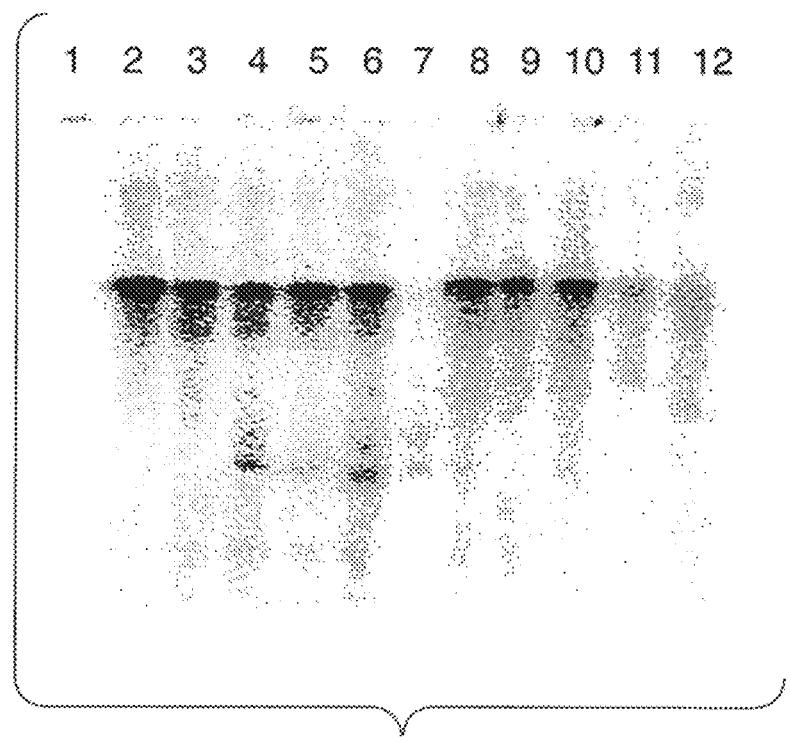

Use examples of the invention are illustrated in greater detail hereinbelow with reference to the figures, in which:

FIG. 1 shows the schematic representation of a plasmid for the in vitro, transcription with T7- and SP6-polymerase, FIG. 2 shows RNA following electrophoresis on an 8% polyacrylamide gel and staining with ethidium bromide, FIG. 3 shows a representation of radioactive RNA transcripts following electrophoresis on an 8% polyacrylamide gel with 7 M urea by means of an instant imager, and FIGS. 4a-e show Texas Red and YFP .fluorescence in murine fibroblasts.

USE EXAMPLE 1

The inhibition of transcription was detected by means of sequence homologous dsRNA in an in vitro transcription system with a nuclear extract from human HeLa cells. The DNA template for this experiment was plasmid pCMV 1200 which had been linearized by means of BamHI.

Generation of the Template Plasmids:

The plasmid shown in FIG. 1 was constructed for use in the enzymatic synthesis of the dsRNA. To this end, a polymerase chain reaction (PCR) with the "positive control DNA" of the HeLaScribe® Nuclear Extract in vitro transcription kit by Promega, Madison, USA, as DNA template was first carried out. One of the primers used contained the sequence of an EcoRI cleavage site and of the T7 RNA polymerase promoter as shown in sequence listing No. 1. The other primer contained the sequence of a BamHI cleavage site and of the SP6 RNA polymerase promoter as shown in sequence listing No. 2. In addition, the two primers had, at the 3' ends, regions which were identical with or complementary to the DNA template. The PCR was carried out by means of the "Taq PCR Core Kits" by Qiagen, Hilden, Germany, following the manufacturer's instructions. 1.5 mM $MgCl_2$, in each case 200 μM dNTP, in each case 0.5 μM primer, 2.5 U Taq DNA polymerase and approximately 100 ng of "positive control DNA" were employed as template in PCR buffer in a volume of 100 μl. After initial denaturation of the template DNA by heating for 5 minutes at 94° C., amplification was carried out in 30 cycles of denaturation for in each case 60 seconds at 94° C., annealing for 60 seconds at 5° C. below the calculated melting point of the primers and polymerization for 1.5-2 minutes at 72° C. After a final polymerization of 5 minutes at 72° C., 5 μl of the reaction were analyzed by agarose-gel electrophoresis. The length of the DNA fragment amplified thus was 400 base pairs, 340 base pairs corresponding to the "positive control DNA". The PCR product was purified, hydrolyzed with EcoRI and BamHI and, after repurification, employed in the ligation together with a pUC18 vector which had also been hydrolyzed by EcoRI and BamHI. *E. coli* XL1-blue was then transformed. The plasmid obtained (pCMV5) carries a DNA fragment whose 5' end is flanked by the T7 promoter and whose 3' end is flanked by the SP6 promoter. By linearizing the plasmid with BamHI, it can be employed in vitro with the T7-RNA polymerase for the run-off transcription of a single-stranded RNA which is 340 nucleotides in length and shown in sequence listing No. 3. If the plasmid is linearized with EcoRI, it can be employed for the run-off transcription with SP6 RNA polymerase, giving rise to the complementary strand. In accordance with the method outlined hereinabove, an RNA 23 nucleotides in length was also synthesized. To this end, a DNA shown in sequence listing No. 4 was ligated with the pUC18 vector via the EcoRI and BamHI cleavage sites.

Plasmid pCMV1200 was constructed as DNA template for the in-vitro transcription with HeLa nuclear extract. To this end, a 1 191 bp EcoRI/BamHI fragment of the positive control DNA contained in the HeLaScribe® Nuclear Extract in vitro transcription kit was amplified by means of PCR. The amplified fragment encompasses the 828 by "immediate early" CMV promoter and a 363 by transcribable DNA fragment. The PCR product was ligated to the vector pGEM-T via "T-overhang" ligation. A BamHI cleavage site is located at the 5' end of the fragment. The plasmid was linearized by hydrolysis with BamHI and used as template in the run-off transcription.

In-Vitro Transcription of the Complementary Single Strands:

pCMV5 plasmid DNA was linearized with EcoRI or BamHI. It was used as DNA template for an in-vitro transcription of the complementary RNA single strands with SP6 and T7 RNA polymerase, respectively. The "Riboprobe in vitro Transcription" system by Promega, Madison, USA, was employed for this purpose. Following the manufacturer's instructions, 2 μg of linearized plasmid DNA were incubated in 100 μl of transcription buffer and 40 U T7 or SP6 RNA polymerase for 5-6 hours at 37° C. The DNA template was subsequently degraded by addition of 2.5 μl of RNase-free DNase RQ1 and incubation for 30 minutes at 37° C. The transcription reaction was made up to 300 μl with $H_2O$ and purified by phenol extraction. The RNA was precipitated by addition of 150 μl of 7 M ammonium acatate [sic] and 1 125 μl of ethanol and stored at −65° C. until used for the hybridization.

Generation of the RNA Double Strands:

For the hybridization, 500 μl of the single-stranded RNA which had been stored in ethanol and precipitated were spun down. The resulting pellet was dried and taken up in 30 μl of PIPES buffer, pH 6.4 in the presence of 80% formamide, 400 mM NaCl and 1 mM EDTA. In each case 15 μl of the complementary single strands were combined and heated for 10 minutes at 85° C. The reactions were subsequently incubated overnight at 50° C. and cooled to room temperature.

Only approximately equimolar amounts of the two single strands were employed in the hybridization. This is why the dsRNA preparations contained single-stranded RNA (ssRNA) as contaminant. In order to remove these ssRNA contaminants, the reactions were treated, after hybridization, with the single-strand-specific ribonucleases bovine pancreatic RNase A and *Aspergillus oryzae* RNase T1. RNase A is an endoribonuclease which is specific for pyrimidines. RNase T1 is an endoribonuclease which preferentially cleaves at the 3' side of guanosines. dsRNA is no substrate for these ribonucleases. For the RNase treatment, the reactions in 300 μl of Tris, pH 7.4, 300 mM NaCl and 5 mM EDTA were treated with 1.2 μl of RNaseA at a concentration of 10 mg/ml and 2 μl of RNaSeT1 at a concentration of 290 μg/ml. The reactions were incubated for 1.5 hours at 30° C. Thereupon, the RNases were denatured by addition of 5 μl of proteinase K at a concentration of 20 mg/ml and 10 μl of 20% SDS and incubation for 30 minutes at 37° C. The dSRNA was purified by phenol extraction and precipitated with ethanol. To verify the completeness of the RNase digestion, two control reactions were treated with ssRNA analogously to the hybridization reactions.

The dried pellet was taken up in 15 μl of TE buffer, pH 6.5, and subjected to native polyacrylamide gel electrophoresis on an 8% gel. The acrylamide gel was subsequently stained in an ethidium bromide solution and washed in a water bath. FIG. 2 shows the RNA which had been visualized in a UV transilluminator. The sense RNA which had been applied to lane 1 and the antisense RNA which had been applied to lane 2 showed a different migration behavior under the chosen conditions than the dsRNA of the hybridization reaction which had been applied to lane 3. The RNase-treated sense RNA and antisense RNA which had been applied to lanes 4 and 5, respectively, produced no visible band. This shows that the single-stranded RNAs had been degraded completely. The RNase-treated dsRNA of the hybridization reaction which had been applied to lane 6 is resistant to RNase treatment. The band which migrates faster in the native gel in comparison with the dsRNA applied to lane 3 results from dsRNA which is free from ssRNA. In addition to the dominant main band, weaker bands which migrate faster are observed after the RNase treatment.

In-Vitro Transcription Test with Human Nuclear Extract:

Using the HeLaScribe® Nuclear Extract in vitro transcription kit by Promega, Madison, USA, the transcription efficiency of the abovementioned DNA fragment which is present in plasmid pCMV1200 and homologous to the "positive control DNA" was determined in the presence of the dsRNA (dsRNA-CMV5) with sequence homology. Also, the effect of the dsRNA without sequence homology, which corresponds to the yellow fluorescent protein (YFP) gene (dsRNA-YRP), was studied. This dsRNA had been generated analogously to the dsRNA with sequence homology. The sequence of a strand of this dsRNA can be found in sequence listing No. 5. Plasmid pCMV1200 was used as template for the run-off transcription. It carries the "immediate early" cytomegalovirus promoter which is recognized by the eukaryotic RNA polymerase II, and a transcribable DNA fragment. Transcription was carried out by means of the HeLa nuclear extract, which contains all the proteins which are necessary for transcription. By addition of [●-$^{32}$P] rGTP to the transcription reaction, radiolabeled transcript was obtained. The [●-$^{32}$P] rGTP used had a specific activity of 400 Ci/mmol, 10 mCi/ml. 3 mM $MgCl_2$, in each case 400 µM rATP, rCTP, rUTP, 16 µM rGTP, 0.4 µM [●-$^{32}$P] rGTP and depending on the experiment 1 fmol of linearized plasmid DNA and various amounts of dsRNA in transcription buffer were employed per reaction. Each batch was made up to a volume of 8.5 µl with $H_2O$. The reactions were mixed carefully. To start the transcription, 4 U HeLa nuclear extract in a volume of 4 µl were added and incubated for 60 minutes at 30° C. The reaction was stopped by addition of 87.5 µl of quench mix which had been warmed to 30° C. To remove the proteins, the reactions were treated with 100 µl of phenol/chloroform/isoamyl alcohol (25:24:1 v/v/v) saturated with TE buffer, pH 5.0, and the reactions were mixed vigorously for 1 minute. For phase separation, the reactions were spun for approximately 1 minute at 12 000 rpm and the top phase was transferred into a fresh reaction vessel. Each reaction was treated with 250 µl of ethanol. The reactions were mixed thoroughly and incubated for at least 15 minutes on dry ice/methanol. To precipitate the RNA, the reactions were spun for 20 minutes at 12 000 rpm and 40° C. The supernatant was discarded. The pellet was dried in vacuo for 15 minutes and resuspended in 10 µl of $H_2O$. Each reaction was treated with 10 µl of denaturing loading buffer. The free GTP was separated from the transcript formed by means of denaturing polyacrylamide gel electrophoresis on an 8% gel with 7 M urea. The RNA transcripts formed upon transcription with HeLa nuclear extract, in denaturing loading buffer, were heated for 10 minutes at 90° C. and 10 µl aliquots were applied immediately to the freshly washed pockets. The electrophoresis was run at 40 mA. The amount of the radioactive ssRNA formed upon transcription was analyzed after electrophoresis with the aid of an Instant Imager.

FIG. 3 shows the radioactive RNA from a representative test, shown by means of the Instant Imager. Samples obtained from the following transcription reactions were applied:

Lane 1: without template DNA, without dsRNA;
Lane 1: 50 ng of template DNA, without dsRNA;
Lane 3: 50 ng of template DNA, 0.5 µg of dsRNA YFP;
Lane 4: 50 ng of template DNA, 1.5 µg of dsRNA YFP;
Lane 5: 50 ng of template DNA, 3 µg of dsRNA: YFP;
Land 6: 50 ng of template DNA, 5 µg of dsRNA YFP;
Lane 7: without template DNA, 1.5 dsRNA YFP;
Lane 8: 50 ng of template DNA, without dsRNA;
Lane 9: 50 ng of template DNA, 0.5 µg of dsRNA CMV5;
Lane 10: 50 ng of template DNA, 1.5 µg of dsRNA CMV5;
Lane 11: 50 ng of template DNA, 3 µg of dsRNA CMV5;
Lane 12: 50 ng of template DNA, 5 µg of dsRNA CMV5;

It emerged that the amount of transcript was reduced markedly in the presence of dsRNA with sequence homology in comparison with the control reaction without dsRNA and with the reactions with dsRNA YFP without sequence homology. The positive control in lane 2 shows that radioactive transcript was formed upon the in-vitro transcription with HeLa nuclear extract. The reaction is used for comparison with the transcription reactions which had been incubated in the presence of dsRNA. Lanes 3 to 6 show that the addition of non-sequentially-specific dsRNA YFP had no effect on the amount of transcript formed. Lanes 9 to 12 show that the addition of an amount of between 1.5 and 3 µg of sequentially-specific dsRNA CMV5 leads to a reduction in the amount of transcript formed. In order to exclude that the effects observed are based not on the dsRNA but on any contamination which might have been carried along accidentally during the preparation of the dsRNA, a further control was carried out. Single-stranded RNA was transcribed as described above and subsequently subjected to the RNase treatment. It was demonstrated by means of native polyacrylamide gel electrophoresis that the ssRNA had been degraded completely. This reaction was subjected to phenol extraction and ethanol precipitation and subsequently taken up in PE buffer, as were the hybridization reactions. This gave a sample which contained no RNA but had been treated with the same enzymes and buffers as the dsRNA. Lane 8 shows that the addition of this sample had no effect on transcription. The reduction of the transcript upon addition of sequence-specific dsRNA can therefore be ascribed unequivocally to the dsRNA itself. The reduction of the amount of transcript of a gene in the presence of dsRNA in a human transcription system indicates an inhibition of the expression of the gene in question. This effect can be attributed to a novel mechanism caused by the dsRNA.

USE EXAMPLE 2

The test system used for these in-vivo experiments was the murine fibroblast cell line NIH3T3, ATCC CRL-1658. The YFP gene was introduced into the nuclei with the aid of microinjection. Expression of YFP was studied under the effect of simultaneously cotransfected dsRNA with sequence homology. This dsRNA YFP shows homology with the 5'-region of the YFP gene over a length of 315 bp. The nucleotide sequence of a strand of the dsRNA YRP is shown in sequence listing No. 5. Evaluation under the fluorescence microscope was carried out 3 hours after injection with reference to the greenish-yellow fluorescence of the YFP formed.

Construction of the Template Plasmid, and Preparation of the dsRNA:

A plasmid was constructed following the same principle as described in use example 1 to act as template for the production of the YFP dsRNA by means of T7 and SP6 in-vitro transcription. Using the primer Eco_T7_YFP as shown in sequence listing No. 6 and Bam_SP6_YFP as shown in sequence listing No. 7, the desired gene fragment was amplified by PCR and used analogously to the above description for preparing the dsRNA. The dsRNA YFP obtained is identical to the dsRNA used in use example 1 as non-sequence-specific control.

A dsRNA linked chemically at the 3' end of the RNA as shown in sequence listing No. 8 to the 5' end of the complementary RNA via a C18 linker group was prepared (L-dsRNA). To this end, synthons modified by disulfide bridges were used. The 3'-terminal synthon is bound to the solid support via the 3' carbon with an aliphatic linker group via a disulfide bridge. In the 5'-terminal synthon of the complementary oligoribonucleotide which is complementary to the 3'-terminal synthon of the one oligoribonucleotide, the 5'-trityl protecting group is bound via a further aliphatic linker and a disulfide bridge. Following synthesis of the two single strands, removal of the protecting groups and hybridization of the complementary oligoribonucleotides, the thiol groups which form are brought into spatial vicinity. The single strands are linked to each other by oxidation via their aliphatic linkers and a disulfide bridge. This is followed by purification with the aid of HPLC.

Preparation of the Cell Cultures:

The cells were incubated in DMEM supplemented with 4.5 g/l glucose, 10% fetal bovine serum in culture dishes at 37° C. under a 7.5% $CO_2$ atmosphere and passaged before reaching confluence. The cells were detached with trypsin/EDTA. To prepare for microinjection, the cells were transferred into Petri dishes and incubated further until microcolonies formed.

Microinjection:

For the microinjection, the culture dishes were removed from the incubator for approximately 10 minutes. Approximately 50 nuclei were injected singly per reaction within a marked area using the AIS microinjection system from Carl Zeiss, Gottingen, Germany. The cells were subsequently incubated for three more hours. For the microinjection, borosilicate glass capillaries from Hilgenberg GmbH, Malsfeld, Germany, with a diameter of less than 0.5 μm at the tip were prepared. The microinjection was carried out using a micromanipulator from Narishige Scientific Instrument Lab., Tokyo, Japan. The injection time was 0.8 seconds and the pressure was approximately 100 hPa. The transfection was carried out using the plasmid pCDNA YFP, which contains an approximately 800 bP BamHI/EcoRI fragment with the YFP gene in vector pcDNA3. The samples injected into the nuclei contained 0.01 μg/μl of pCDNA-YFP and Texas Red coupled to dextran-70000 in 14 mM NaCl, 3 mM KCl, 10 mM $KPO_4$ [sic], ph 7.5. Approximately 100 pl of RNA with a concentration of 1 μM or, in the case of the L-dsRNA, 375 μM were additionally added.

The cells were studied under a fluorescence microscope with excitation with the light of the excitation wavelength of Texas Red, 568 nm, or of YFP, 488 nm. Individual cells were documented by means of a digital carvers. FIGS. 4a-e show the result for NIH3T3 cells. In the cells shown in FIG. 4a, sense-YFP-ssRNA has been injected, in FIG. 4b antisense-YFP-ssRNA, in FIG. 4c dsRNA-YFP, in FIG. 4d no RNA and in FIG. 4e L-dsRNA.

The field on the left shows in each case the fluorescence of cells with excitation at 568 nm. The fluorescence of the same cells at an excitation of 488 nm is seen on the right. The Texas Red fluorescence of all the cells shown demonstrates that the injection solution had been applied successfully into the nuclei and that cells with successful hits were still alive after three hours. Dead cells no longer showed Texas Red fluorescence.

Figure 4A:
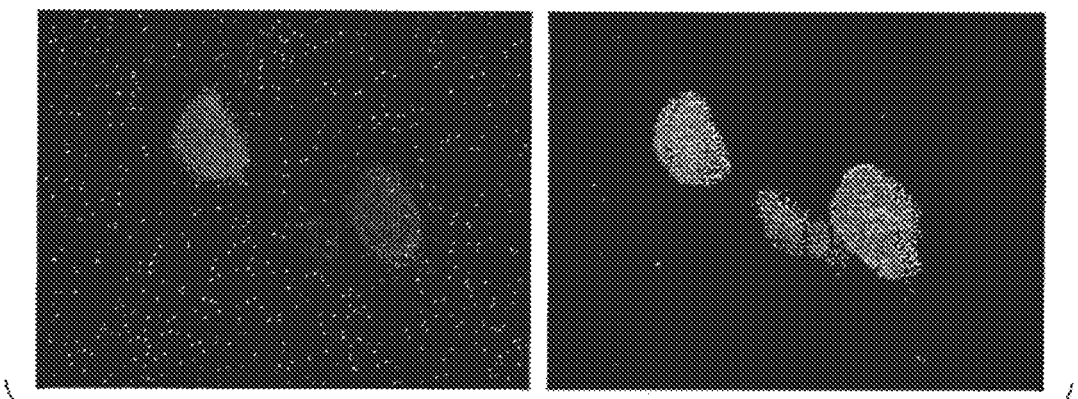
Figure 4B:
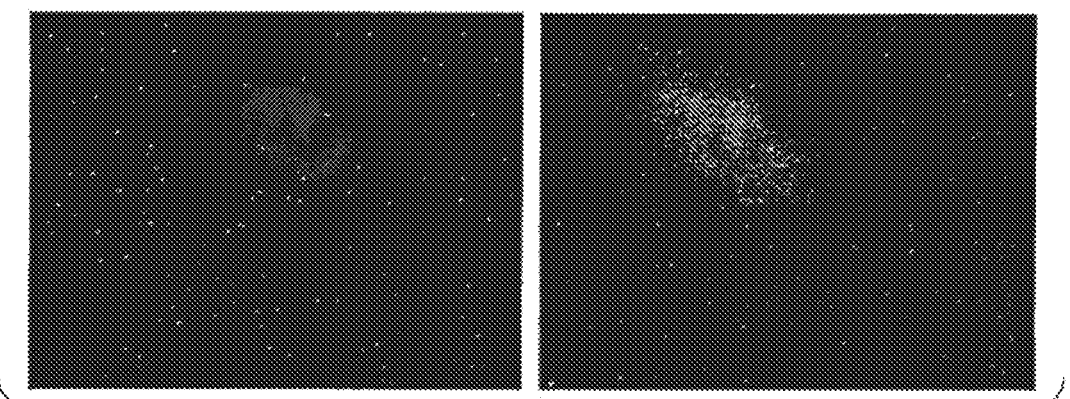
Figure 4C:
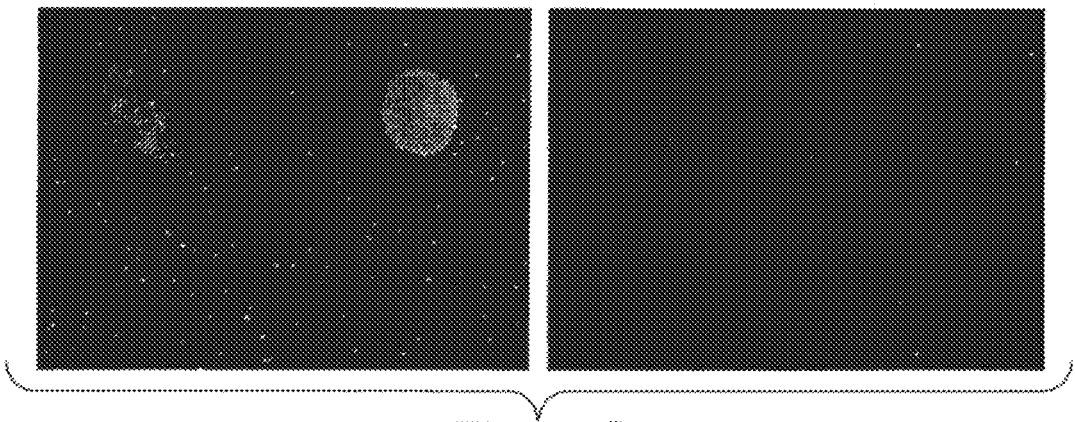
Figure 4D:
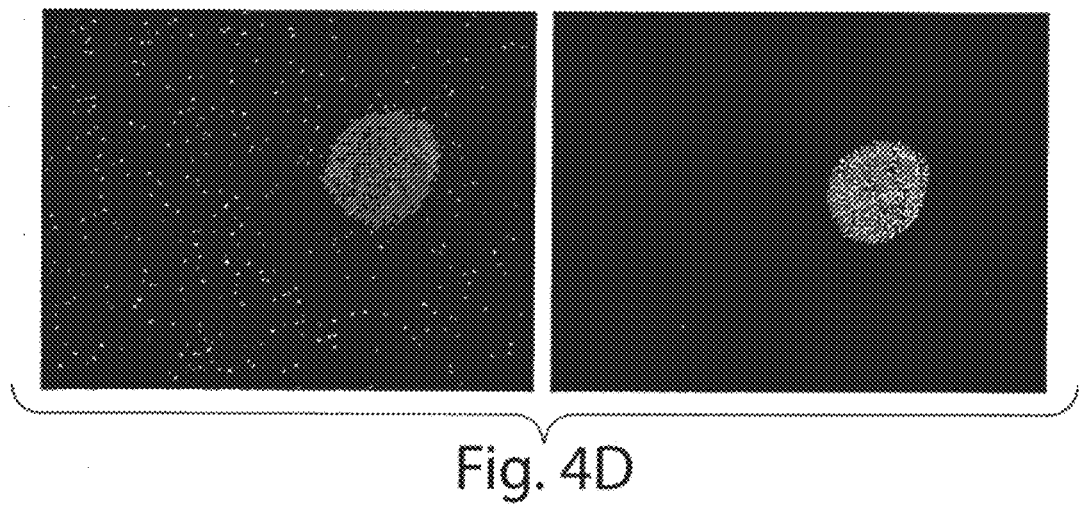
Figure 4E:
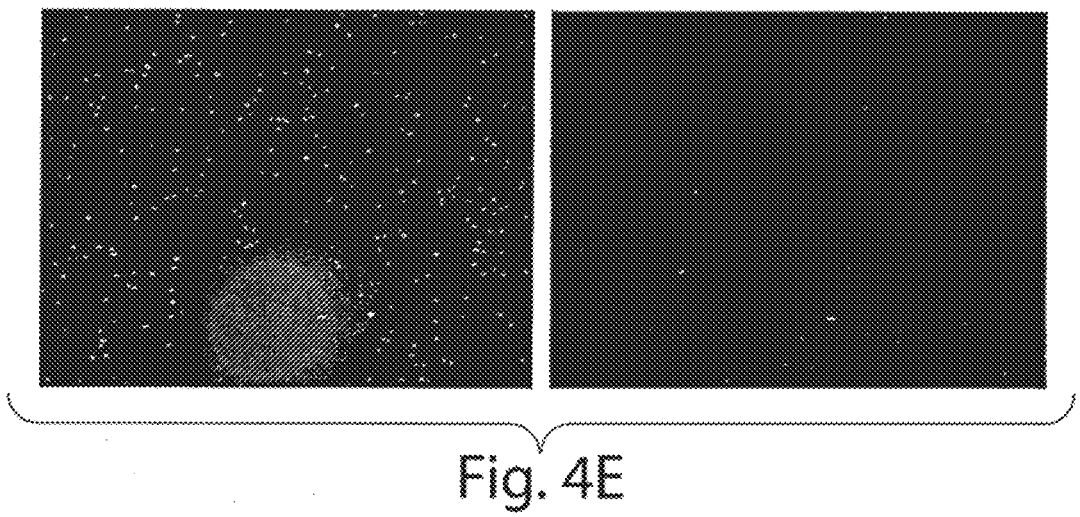

The right fields of each of FIGS. 4a and 4b show that YFP expression was not visibly inhibited when the single-stranded RNA was injected into the nuclei. The right field of FIG. 4c shows cells whose YFP fluorescence was no longer detectable after the injection of dsRNA-YFP. FIG. 4d shows cells into which no RNA had been injected, as control. The cell shown in FIG. 4e shows YFP fluorescence which can no longer be detected owing to the injection of the L-dsRNA which shows regions with sequence homology to the YFP gene. This result demonstrates that even shorter dsRNAs can be used for specifically inhibiting gene expression in mammals when the double strands are stabilized by chemically linking the single strands.

The invention claimed is:

1. A composition comprising two oligoribonucleotides of double-stranded structure (dsRNAs), each dsRNA for inhibiting the expression of a distinct target gene in mammalian cells, wherein the two dsRNAs are capable of being introduced into the cell simultaneously, and wherein each dsRNA has 15 to 49 base pairs and has a complementary region I that is incorporated in the respective dsRNA.

2. The composition of claim 1, wherein at least one strand of each dsRNA comprises at least one chemically modified nucleotide.

3. The composition of claim 2, wherein the chemically modified nucleotide is a 2'-modified nucleotide.

4. The composition of claim 3, wherein the 2'-modified nucleotide is a 2'-methyl substituted nucleotide.

5. The composition of claim 3, wherein the 2'-modified nucleotide is a 2'-amino substituted nucleotide.

6. The composition of claim 2, wherein the chemically modified nucleotide is a locked nucleotide.

7. The composition of claim 1, wherein the target genes are mammalian genes or viral genes.

8. The composition of claim 1, wherein the target genes are selected from the group consisting of an oncogene, a cytokine gene, an Id protein gene, a developmental gene, a PKR gene and a prion gene.

9. The composition of claim 1, wherein the dsRNAs are enclosed by a micellar structure.

10. The composition of claim 9, wherein the micellar structure comprises a liposome.

11. The composition of claim 1, wherein an end of each dsRNA is modified in order for the double-stranded structure to counteract degradation.

12. The composition of claim 1, wherein each dsRNA comprises a sense strand and an antisense strand, and wherein each sense strand comprises a 2'-methyl substituted nucleotide.

13. The composition of claim 1, wherein each dsRNA comprises a sense strand and an antisense strand, and wherein each sense strand comprises a 2'-methoxynucleotide.

14. The composition of claim 1, wherein each dsRNA comprises a sense strand and an antisense strand, and wherein each sense strand comprises a plurality of 2'-methoxynucleotides.

15. The composition of claim 1, wherein the dsRNAs comprise a pharmaceutical composition formulated for delivery to a mammalian cell.

16. The composition of claim 1, wherein one of the distinct target genes is a double-stranded-RNA-dependent protein kinase (PKR).

* * * * *